(12) United States Patent
Cao et al.

(10) Patent No.: US 10,820,882 B2
(45) Date of Patent: Nov. 3, 2020

(54) METHODS FOR DETERMINING MISALIGNMENT OF X-RAY DETECTORS

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

(*) Notice: Subject to any disclaimer, the term of this patent is extended or adjusted under 35 U.S.C. 154(b) by 174 days.

(21) Appl. No.: 16/117,867

(22) Filed: Aug. 30, 2018

(65) Prior Publication Data

US 2019/0015068 A1 Jan. 17, 2019

Related U.S. Application Data

(63) Continuation of application No. PCT/CN2016/085407, filed on Jun. 12, 2016.

(51) Int. Cl.
*A61B 6/00* (2006.01)

(52) U.S. Cl.
CPC ............ *A61B 6/585* (2013.01); *A61B 6/4233* (2013.01); *A61B 6/4266* (2013.01); *A61B 6/4241* (2013.01); *A61B 6/584* (2013.01)

(58) Field of Classification Search
CPC ... A61B 6/4233; A61B 6/4241; A61B 6/4266; A61B 6/584; A61B 6/585; G01T 1/242
See application file for complete search history.

(56) References Cited

U.S. PATENT DOCUMENTS

| | | | | |
|---|---|---|---|---|
| 5,307,396 A | * | 4/1994 | Tsuchino | A61B 6/00 378/146 |
| 5,436,958 A | | 7/1995 | Taylor | |
| 6,151,383 A | * | 11/2000 | Xue | A61B 6/00 378/108 |
| 2007/0041508 A1 | * | 2/2007 | Tubbs | A61B 6/583 378/207 |
| 2009/0046913 A1 | * | 2/2009 | Chandra | A61B 6/035 382/131 |
| 2010/0020924 A1 | * | 1/2010 | Steadman Booker | G01T 1/2928 378/19 |
| 2010/0252742 A1 | | 10/2010 | Tkaczyk | |
| 2013/0083887 A1 | * | 4/2013 | Li | A61B 6/4266 378/19 |
| 2016/0148398 A1 | * | 5/2016 | Takemoto | A61B 6/5264 378/63 |

FOREIGN PATENT DOCUMENTS

| | | |
|---|---|---|
| CN | 1915169 A | 2/2007 |
| CN | 102135626 A | 7/2011 |
| CN | 102177585 A | 9/2011 |
| JP | 2013142578 A * | 7/2013 |

* cited by examiner

*Primary Examiner* — Chih-Cheng Kao
(74) *Attorney, Agent, or Firm* — IPro, PLLC

(57) ABSTRACT

Disclosed herein is a method comprising: obtaining a third image from a first X-ray detector when the first X-ray detector and a second X-ray detector are misaligned; determining, based on a shift between a first image and the third image, a misalignment between the first X-ray detector and the second X-ray detector when the first and second detectors are misaligned; wherein the first image is an image the first X-ray detector should capture if the first and the second detectors are aligned.

22 Claims, 42 Drawing Sheets

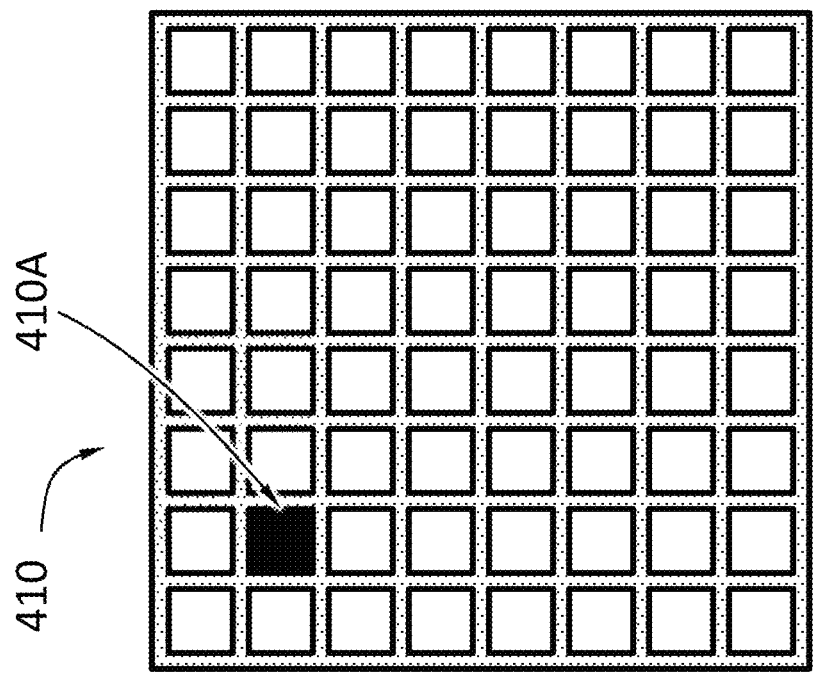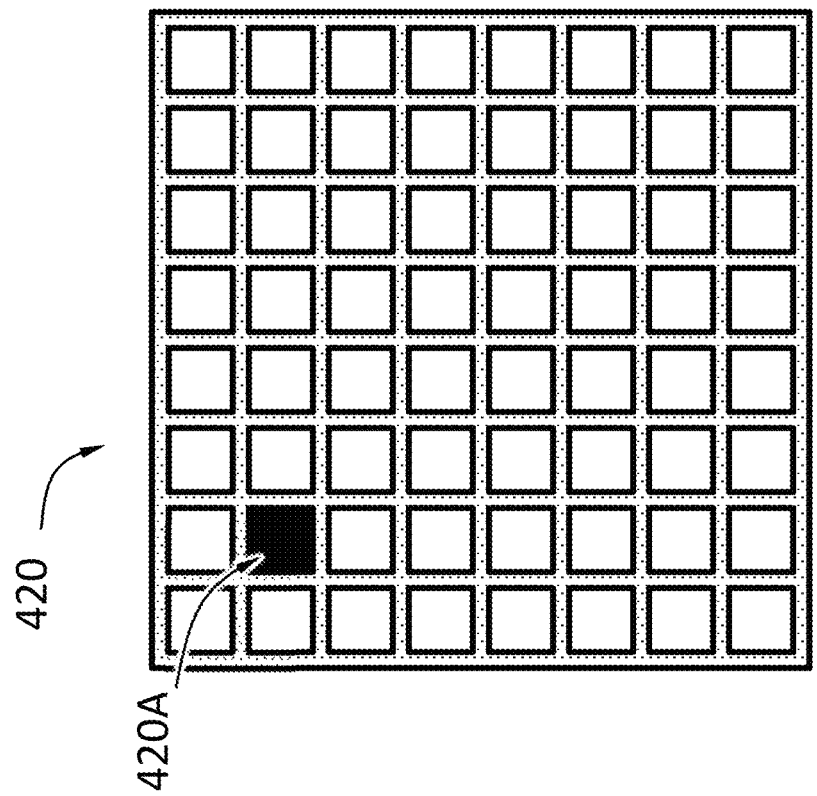
Fig. 4B

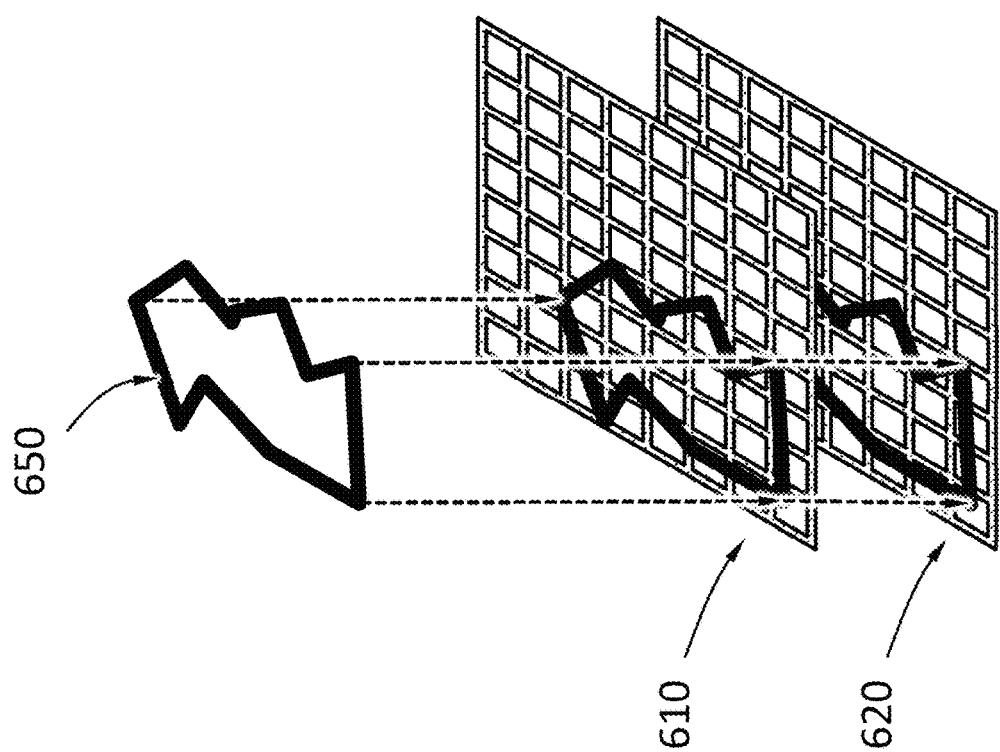

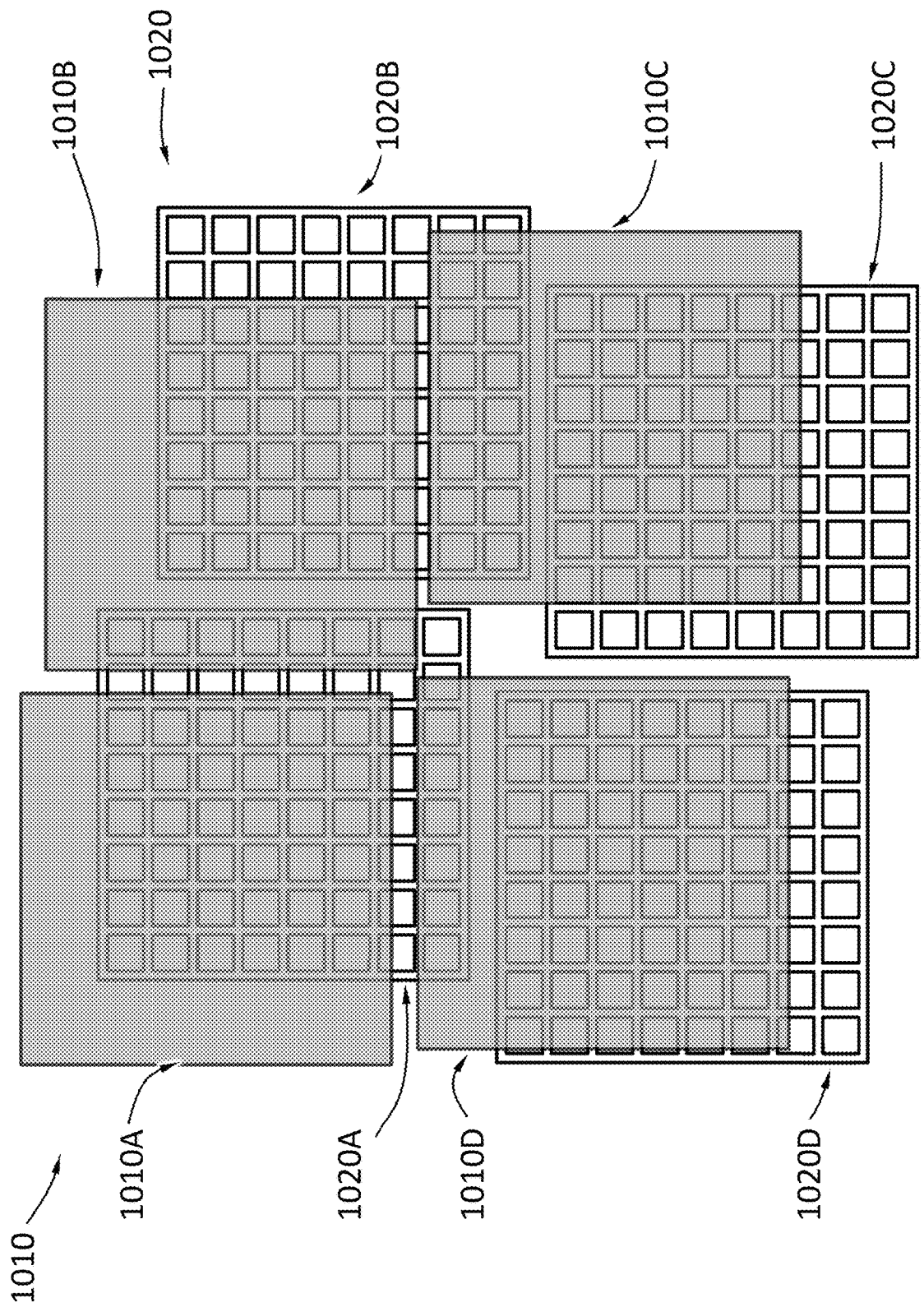

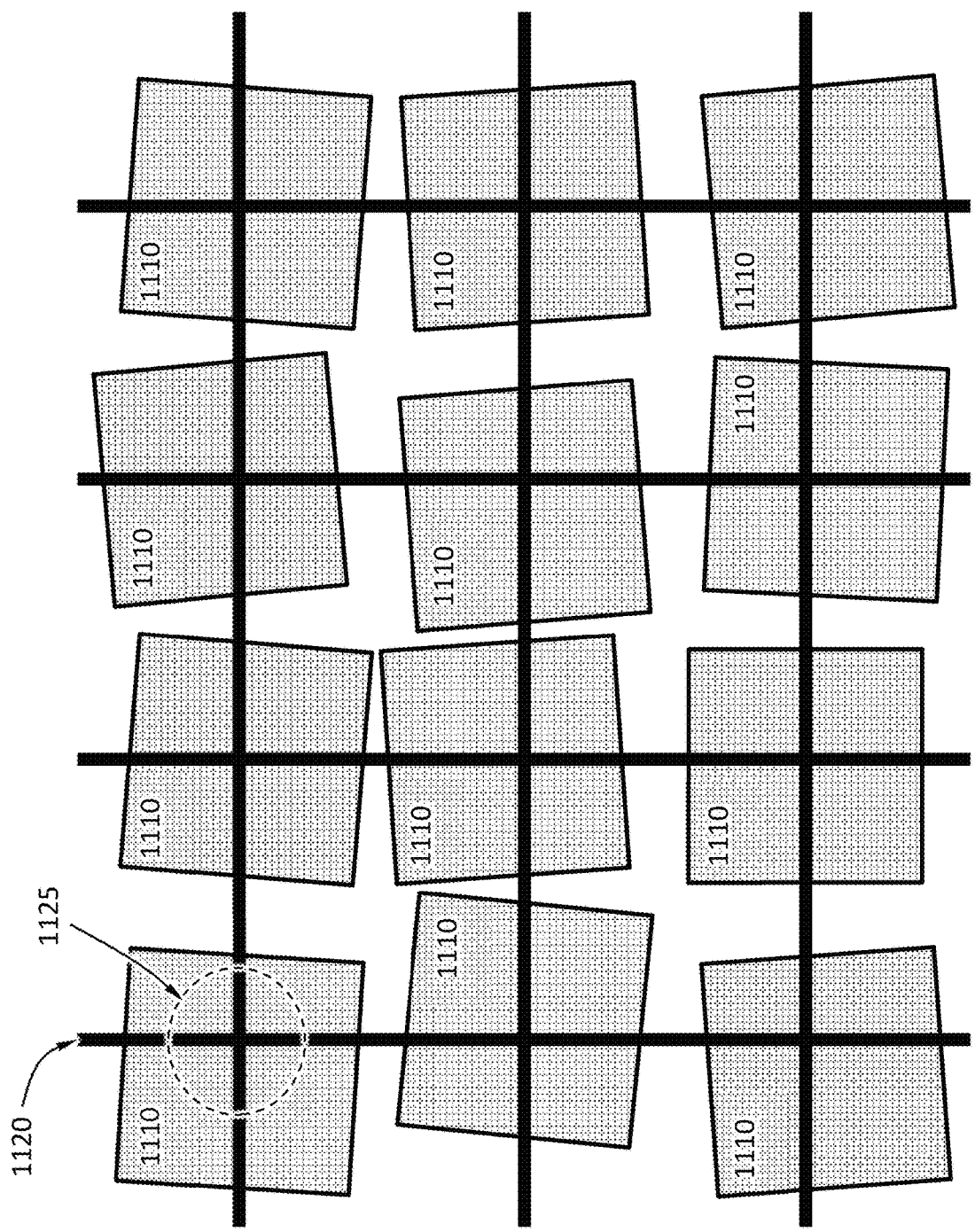

METHODS FOR DETERMINING MISALIGNMENT OF X-RAY DETECTORS

TECHNICAL FIELD

The disclosure herein relates to X-ray detectors, particularly relates to methods for determining misalignment of X-ray detectors.

BACKGROUND

X-ray detectors may be devices used to measure the flux, spatial distribution, spectrum or other properties of X-rays.

X-ray detectors may be used for many applications. One important application is imaging. X-ray imaging is a radiography technique and can be used to reveal the internal structure of a non-uniformly composed and opaque object such as the human body.

Early X-ray detectors for imaging include photographic plates and photographic films. A photographic plate may be a glass plate with a coating of light-sensitive emulsion. Although photographic plates were replaced by photographic films, they may still be used in special situations due to the superior quality they offer and their extreme stability. A photographic film may be a plastic film (e.g., a strip or sheet) with a coating of light-sensitive emulsion.

In the 1980s, photostimulable phosphor plates (PSP plates) became available. A PSP plate may contain a phosphor material with color centers in its lattice. When the PSP plate is exposed to X-ray, electrons excited by X-ray are trapped in the color centers until they are stimulated by a laser beam scanning over the plate surface. As the plate is scanned by laser, trapped excited electrons give off light, which is collected by a photomultiplier tube. The collected light is converted into a digital image. In contrast to photographic plates and photographic films, PSP plates can be reused.

Another kind of X-ray detectors are X-ray image intensifiers. Components of an X-ray image intensifier are usually sealed in a vacuum. In contrast to photographic plates, photographic films, and PSP plates, X-ray image intensifiers may produce real-time images, i.e., not requiring post-exposure processing to produce images. X-ray first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident X-ray. The emitted electrons are projected, through electron optics, onto an output phosphor and cause the output phosphor to produce a visible-light image.

Scintillators operate somewhat similarly to X-ray image intensifiers in that scintillators (e.g., sodium iodide) absorb X-ray and emit visible light, which can then be detected by a suitable image sensor for visible light. In scintillators, the visible light spreads and scatters in all directions and thus reduces spatial resolution. Reducing the scintillator thickness helps to improve the spatial resolution but also reduces absorption of X-ray. A scintillator thus has to strike a compromise between absorption efficiency and resolution.

Semiconductor X-ray detectors largely overcome this problem by a direct conversion of X-ray into electric signals. A semiconductor X-ray detector may include a semiconductor layer that absorbs X-ray in wavelengths of interest. When an X-ray photon is absorbed in the semiconductor layer, multiple charge carriers (e.g., electrons and holes) are generated and swept under an electric field towards electrical contacts on the semiconductor layer. Cumbersome heat management required in currently available semiconductor X-ray detectors (e.g., Medipix) can make a detector with a large area and a large number of pixels difficult or impossible to produce.

SUMMARY

Disclosed herein is a method comprising: obtaining a third image from a first X-ray detector when the first X-ray detector and a second X-ray detector are misaligned; determining, based on a shift between a first image and the third image, a misalignment between the first X-ray detector and the second X-ray detector; wherein the first image is an image the first X-ray detector should capture if the first and the second detectors are aligned.

According to an embodiment, the method further comprises obtaining a fourth image from the second X-ray detector when the first X-ray detector and the second X-ray detector are misaligned; wherein determining the misalignment is further based on a shift between a second image and the fourth image; wherein the second image is an image the second X-ray detector should capture if the first and the second detectors are aligned.

According to an embodiment, the first X-ray detector and the second X-ray detector are stacked.

According to an embodiment, the first and third images are formed from a beam of X-ray directed to the first X-ray detector.

According to an embodiment, a part of the beam is absorbed by the first X-ray detector and another part of the beam passes through the first X-ray detector.

According to an embodiment, the first and third images are formed from a scene of X-ray.

According to an embodiment, the first and third images are images of one or more structures of the second X-ray detector.

According to an embodiment, the one or more structures are gaps between pixels.

According to an embodiment, the one or more structures are solder bumps.

According to an embodiment, the first X-ray detector and the second X-ray detector are arranged side by side.

According to an embodiment, the first and third images are formed from a first beam of X-ray directed to the first X-ray detector.

According to an embodiment, the first image is an image of a part of a scene of X-ray.

According to an embodiment, the first X-ray detector has multiple pixels.

According to an embodiment, the first X-ray detector comprises: an X-ray absorption layer comprising an electrode; an electronics layer comprising an electronics system.

According to an embodiment, the electronics system comprises: a first voltage comparator configured to compare a voltage of the electrode to a first threshold; a second voltage comparator configured to compare the voltage to a second threshold; a counter configured to register a number of X-ray photons reaching the X-ray absorption layer; a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the number registered by the counter to increase by one, if the second voltage comparator determines that an absolute value of the voltage equals or exceeds an absolute value of the second threshold.

According to an embodiment, the electronics system further comprises a capacitor module electrically connected to the electrode of the first X-ray absorption layer, wherein the capacitor module is configured to collect charge carriers from the electrode of the first X-ray absorption layer.

According to an embodiment, the controller is configured to activate the second voltage comparator at a beginning or expiration of the time delay.

According to an embodiment, the electronics system further comprises a voltmeter, wherein the controller is configured to cause the voltmeter to measure the voltage upon expiration of the time delay.

According to an embodiment, the controller is configured to determine an X-ray photon energy based on a value of the voltage measured upon expiration of the time delay.

According to an embodiment, the controller is configured to connect the electrode of the first X-ray absorption layer to an electrical ground.

According to an embodiment, a rate of change of the voltage is substantially zero at expiration of the time delay.

According to an embodiment, a rate of change of the voltage is substantially non-zero at expiration of the time delay.

According to an embodiment, the X-ray absorption layer comprises a diode.

Disclosed herein is a method comprising: obtaining a misalignment between a first chip and a second chip; obtaining a misalignment between a third chip and a fourth chip; wherein the first chip, the second chip, the third chip and the fourth chip each are part of a first X-ray detector or a second X-ray detector; wherein the first and second X-ray detectors are stacked; wherein the first chip and the fourth chip do not overlap; determining a misalignment between the first chip and fourth chip using the misalignment between the first chip and the second chip and using the misalignment between the third chip and the fourth chip.

According to an embodiment, the first and fourth chips are part of the same X-ray detector.

According to an embodiment, the second chip and the third chip are the same chip.

According to an embodiment, the second chip and the third chip do not overlap.

Disclosed herein is a method comprising: obtaining an image of one cross pattern among a plurality of cross patterns of a scene, by one chip of a plurality of chips of an X-ray detector; determining a relative position of the one chip relative to the one cross pattern from the image; wherein relative positions of the plurality of cross patterns are known with respect to one another.

According to an embodiment, the one chip is shifted or rotated relative to the one cross pattern.

According to an embodiment, the one cross pattern comprises two lines with finite widths.

According to an embodiment, determining the relative position comprises determining two positions of the one chip, wherein the two positions are on one of the two lines.

According to an embodiment, determining the relative position comprises fitting intensities detected by at least some pixels of the one chip as a function of location of the one chip.

BRIEF DESCRIPTION OF FIGURES

FIG. 4B schematically shows images the X-ray detectors of FIG. 4A should capture if the X-ray detectors are aligned.

FIG. 6A schematically shows that two stacked X-ray detectors and are aligned.

FIG. 10 schematically shows that non-overlapping chips of stacked X-ray detectors may be determined using a chain of overlapping chips.

FIG. 11A schematically shows that misalignment of chips of an X-ray detector with respect to one another may be determined using a scene with multiple cross patterns.

DETAILED DESCRIPTION

Each of PCT Applications Nos. PCT/CN2015/075950, PCT/CN2015/075941, PCT/CN2015/075944, PCT/CN2015/081126, PCT/CN2016/073034, PCT/CN2015/075950, PCT/CN2015/089103, PCT/CN2015/088220, PCT/CN2015/089552, PCT/CN2015/091509, PCT/CN2015/091928, PCT/CN2015/091927, PCT/CN2015/091943, PCT/CN2015/096192 and PCT/CN2016/074663 is hereby incorporated by reference in its entirety.

Figure 1A:
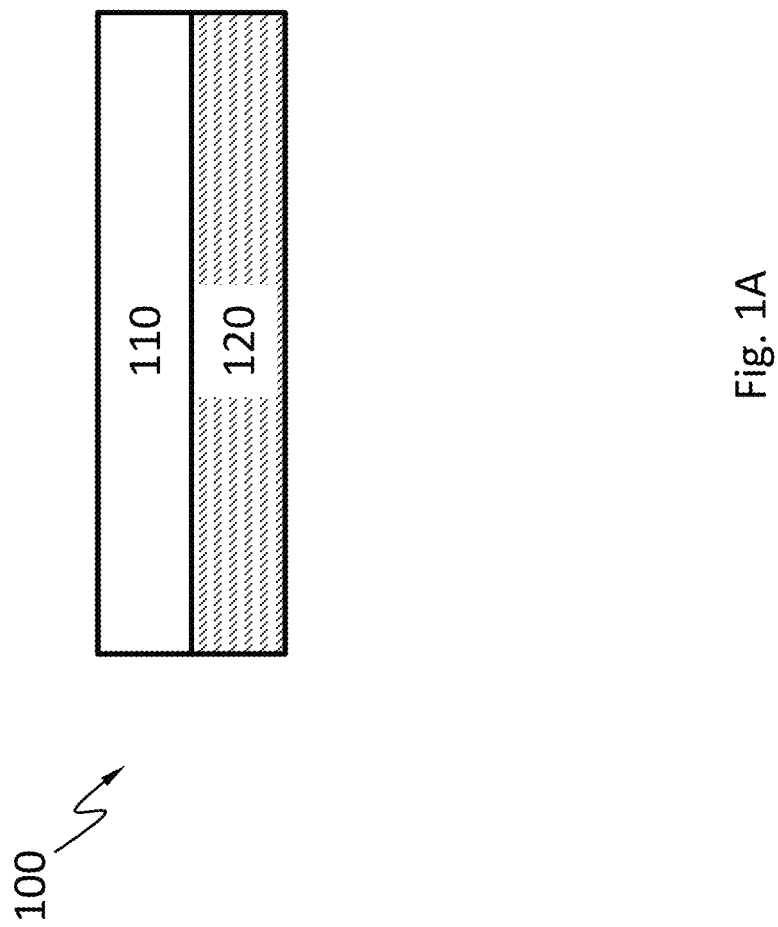
FIG. 1A schematically shows a cross-sectional view of an X-ray detector, according to an embodiment of the present teaching.

FIG. 1A schematically shows a semiconductor X-ray detector 100, according to an embodiment. The semiconductor X-ray detector 100 may include an X-ray absorption layer 110 and an electronics layer 120 (e.g., an ASIC) for processing or analyzing electrical signals incident X-ray generates in the X-ray absorption layer 110. In an embodiment, the semiconductor X-ray detector 100 does not comprise a scintillator. The X-ray absorption layer 110 may include a semiconductor material such as, silicon, germanium, GaAs, CdTe, CdZnTe, or a combination thereof. The semiconductor may have a high mass attenuation coefficient for the X-ray energy of interest.

Figure 1B:
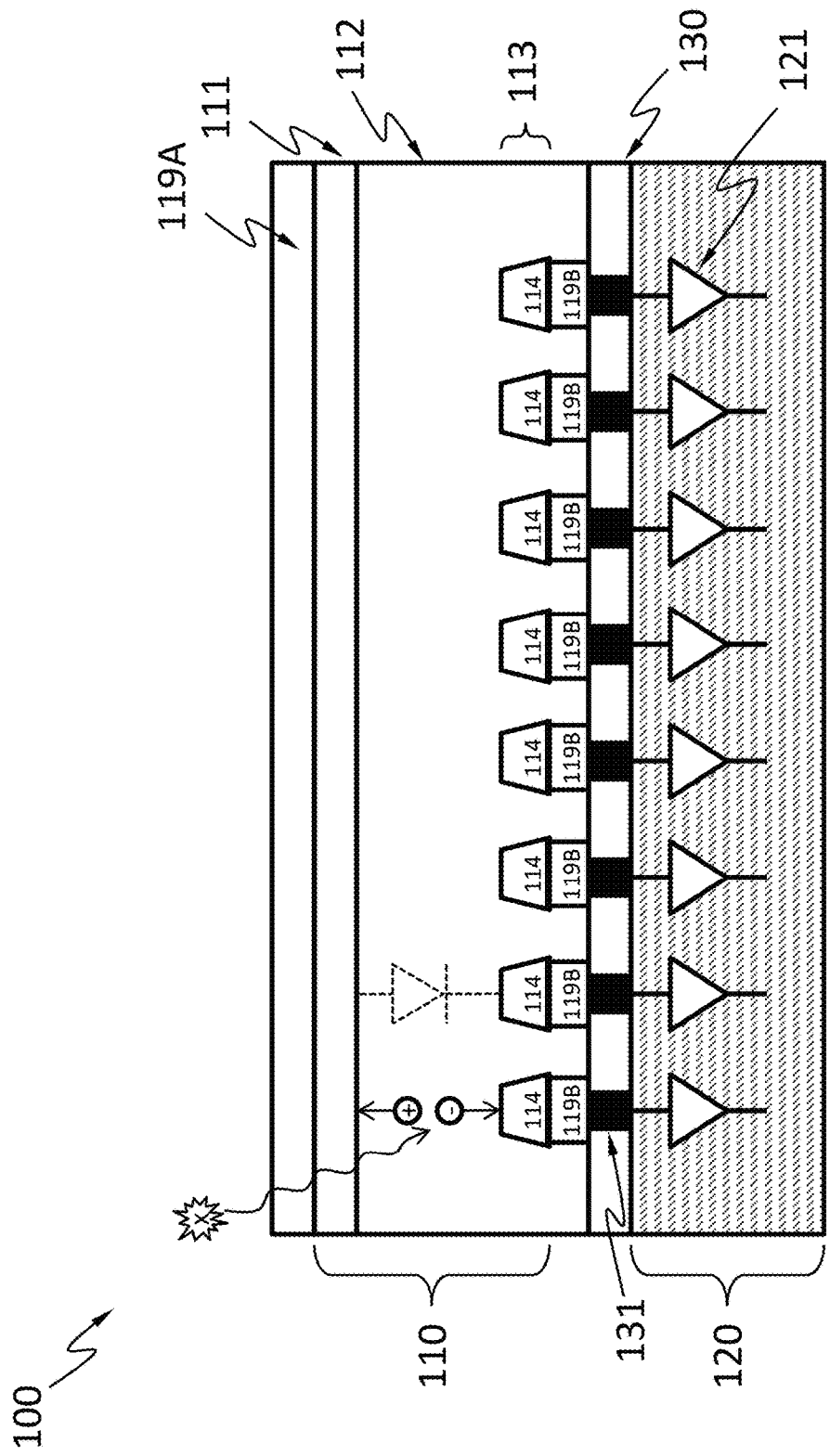
FIG. 1B schematically shows a detailed cross-sectional view of the X-ray detector, according to an embodiment of the present teaching.

As shown in a detailed cross-sectional view of the detector 100 in FIG. 1B, according to an embodiment, the X-ray absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete regions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 1B, each of the discrete regions 114 of the second doped region 113 forms a diode with the first doped region 111 and the optional intrinsic region 112. Namely, in the example in FIG. 1B, the X-ray absorption layer 110 has a plurality of diodes having the first doped region 111 as a shared electrode. The first doped region 111 may also have discrete portions.

When an X-ray photon hits the X-ray absorption layer 110 including diodes, the X-ray photon may be absorbed and generate one or more charge carriers by a number of mechanisms. The charge carriers may drift to the electrodes of one of the diodes under an electric field. The field may be an external electric field. The electrical contact 119B may include discrete portions each of which is in electrical contact with the discrete regions 114.

Figure 1C:
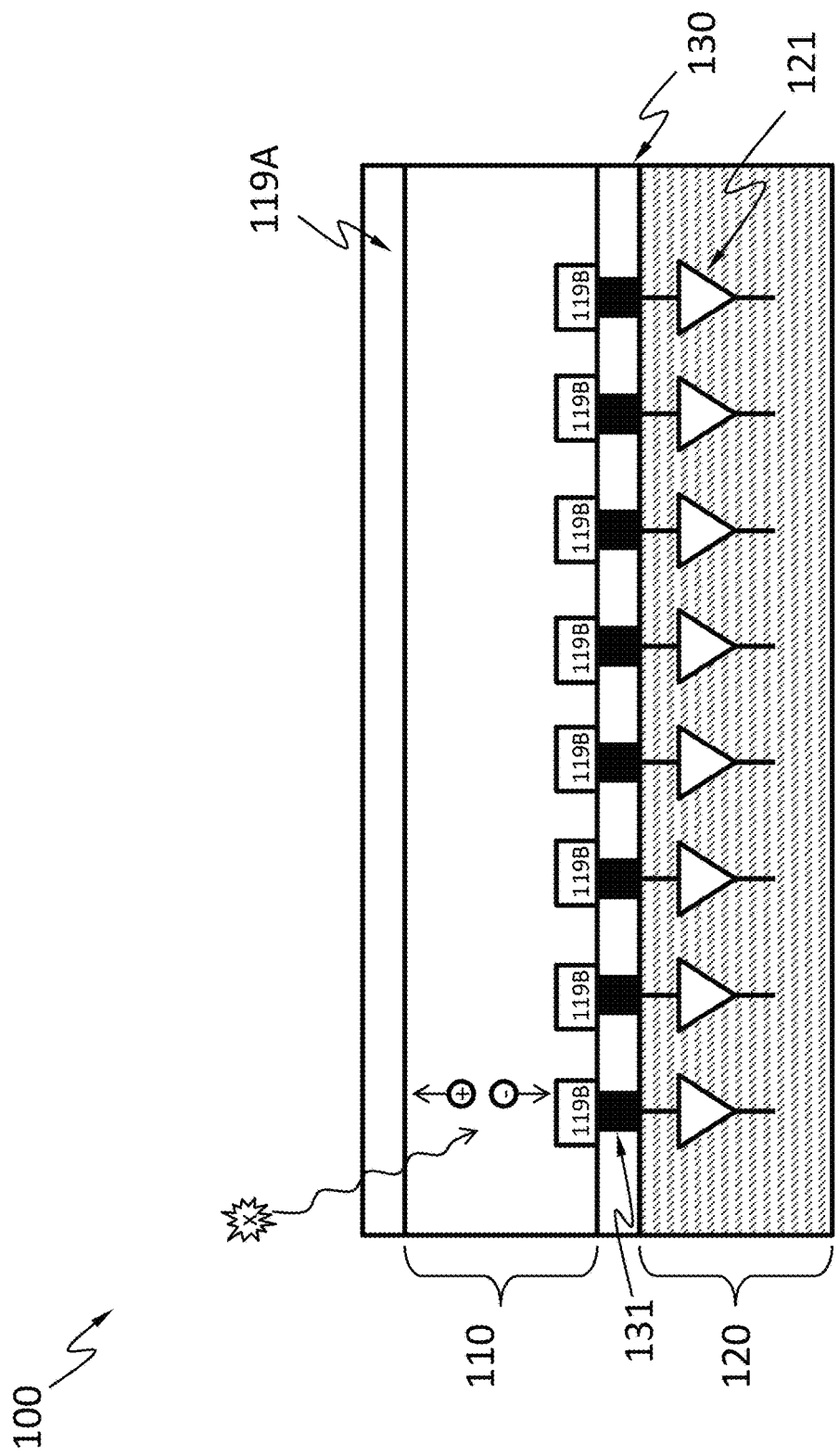
FIG. 1C schematically shows an alternative detailed cross-sectional view of the X-ray detector, according to an embodiment of the present teaching.

As shown in an alternative detailed cross-sectional view of the detector 100 in FIG. 1C, according to an embodiment, the X-ray absorption layer 110 may include a resistor of a semiconductor material such as, silicon, germanium, GaAs, CdTe, CdZnTe, or a combination thereof, but does not include a diode.

When an X-ray photon hits the X-ray absorption layer 110 including a resistor but not diodes, it may be absorbed and generate one or more charge carriers by a number of mechanisms. The charge carriers may drift to the electrical contacts 119A and 119B under an electric field. The electrical contact 119B includes discrete portions.

The electronics layer 120 may include an electronics system 121 suitable for processing or interpreting signals generated by X-ray photons incident on the X-ray absorption layer 110. The electronics system 121 may include an analog circuitry such as a filter network, amplifiers, integrators, and comparators, or a digital circuitry such as a microprocessors, and memory. The electronics system 121 may include components shared by the pixels or components dedicated to a single pixel. For example, the electronics system 121 may include an amplifier dedicated to each pixel and a microprocessor shared among all the pixels. The electronics system 121 may be electrically connected to the pixels by vias 131. Space among the vias may be filled with a filler material 130, which may increase the mechanical stability of the connection of the electronics layer 120 to the X-ray absorption layer 110. Other bonding techniques are possible to connect the electronics system 121 to the pixels without using vias.

Figure 1D:
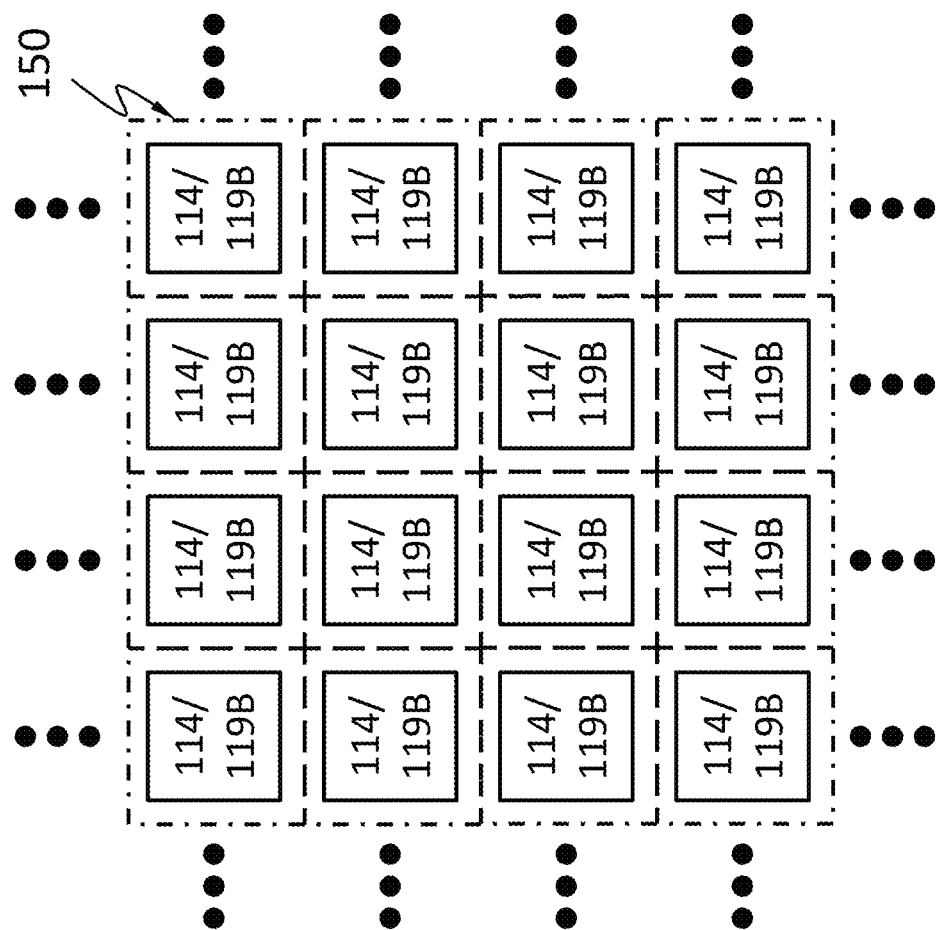
FIG. 1D shows an exemplary top view of a portion of the X-ray detector, according to an embodiment of the present teaching.

FIG. 1D shows an exemplary top view of a portion of the semiconductor X-ray detector 100 with a 4-by-4 array of discrete regions 114/119B. Charge carriers generated by an X-ray photon incident around the footprint of one of these discrete regions 114/119B are not substantially shared with another of these discrete regions 114/119B. The area 150 around a discrete region 114/119B in which substantially all (more than 95%, more than 98% or more than 99% of) charge carriers generated by an X-ray photon incident therein flow to the discrete region 114/119B is called a pixel associated with that discrete region 114/119B. Namely, less than 5%, less than 2% or less than 1% of these charge carriers flow beyond the pixel, when the X-ray photon hits inside the pixel. By measuring the rate of change of the voltage of each of the discrete regions 114/119B, the number of X-ray photons absorbed (which relates to the incident X-ray intensity) and/or the energies thereof in the pixels associated with the discrete regions 114/119B may be determined. Thus, the spatial distribution (e.g., an image) of incident X-ray intensity may be determined by individually measuring the rate of change of the voltage of each one of an array of discrete regions 114/119B. The pixels may be organized in any suitable array, such as, a square array, a triangular array and a honeycomb array. The pixels may have any suitable shape, such as, circular, triangular, square, rectangular, and hexagonal. The pixels may be individually addressable.

Figure 2:
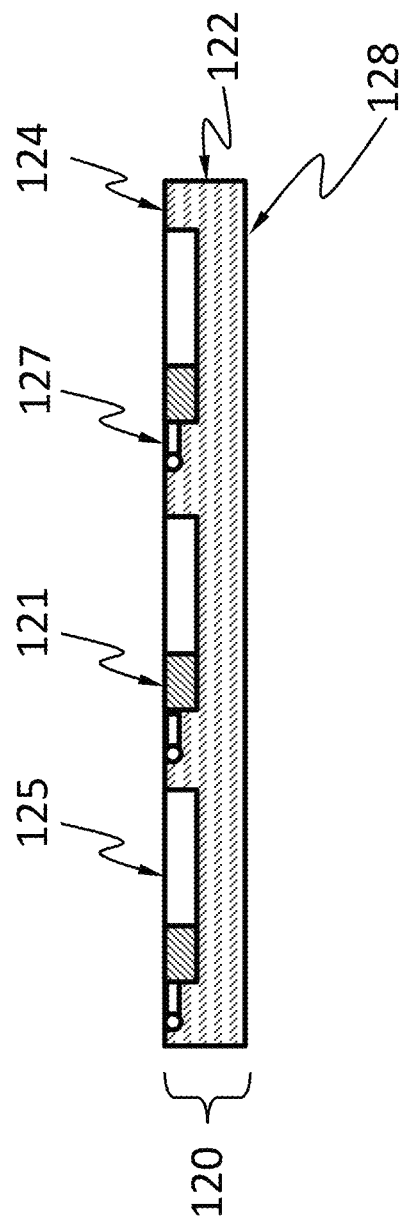
FIG. 2 schematically shows a cross-sectional view of an electronics layer in the X-ray detector, according to an embodiment of the present teaching.

FIG. 2 schematically shows a cross-sectional view of an electronics layer 120 in the detector, according to an embodiment of the present teaching. In this example, the electronics layer 120 comprises a substrate 122 having a first surface 124 and a second surface 128. A "surface" as used herein is not necessarily exposed, but can be buried wholly or partially. The electronics layer 120 comprises one or more electric contacts 125 on the first surface 124. The one or more electric contacts 125 may be configured to be electrically connected to one or more electrodes of the X-ray absorption layer 110. The electronics system 121 may be in or on the substrate 122, and electrically connected to the electric contacts 125.

The electronics layer 120 comprises one or more transmission lines 127 electrically connected to the electronics system 121. The transmission line 127 may be a metal wire on the first surface 124, such that data processed by the electronics system 121 may be read out via the transmission line 127. The transmission line 127 may also be used for control, providing power or input to the electronics system 121.

As shown in FIG. 2, there is no electrical component on the second surface 128, i.e. the bottom side of the substrate 122 does not have electrical components. Therefore, the substrate 122 can be thinned (e.g., by grinding the second surface 128). For example, the substrate may have a thickness of 750 microns or less, 200 microns or less, 100 microns or less, 50 microns or less, 20 microns or less, or 5 microns or less. The substrate 122 may be a silicon substrate or a substrate or other suitable semiconductor or insulator. The substrate 122 may be produced by grinding a thicker substrate to a desired thickness.

The one or more electric contacts 125 may be a layer of metal or doped semiconductor. For example, the electric contacts 125 may be gold, copper, platinum, palladium, doped silicon, etc.

The transmission lines 127 electrically connect electrical components (e.g., the electronics system 121) in the substrate 122 to bonding pads at other locations on the substrate 122. In one embodiment, each transmission lines 127 may be electrically connected to the electronics system 121 through a via. The transmission lines 127 may be electrically isolated from the substrate 122 except at certain vias and certain bonding pads. The transmission lines 127 may be a material (e.g., Al) with small mass attenuation coefficient for the X-ray energy of interest. The transmission lines 127 may redistribute electrical connections to more convenient locations.

An X-ray detector may be stacked over another X-ray detector for various reasons. One of such reasons is to enhance the overall absorption of the incident X-ray, when one X-ray detector cannot absorb all the incident X-ray. An X-ray detector, due to its ability to sense an image formed by the incident X-ray, may have spatial resolution of a characteristic of the X-ray incident on the X-ray detector. Namely, the X-ray detector may have the ability to measure the spatial dependence of the characteristic. The characteristic is usually intensity but is not necessarily intensity. Examples of the characteristic may include phase, polarization, wavelength and frequency. FIGS. 1A-1D and FIG. 2 show such an X-ray detector with spatial resolution.

Figure 3A:
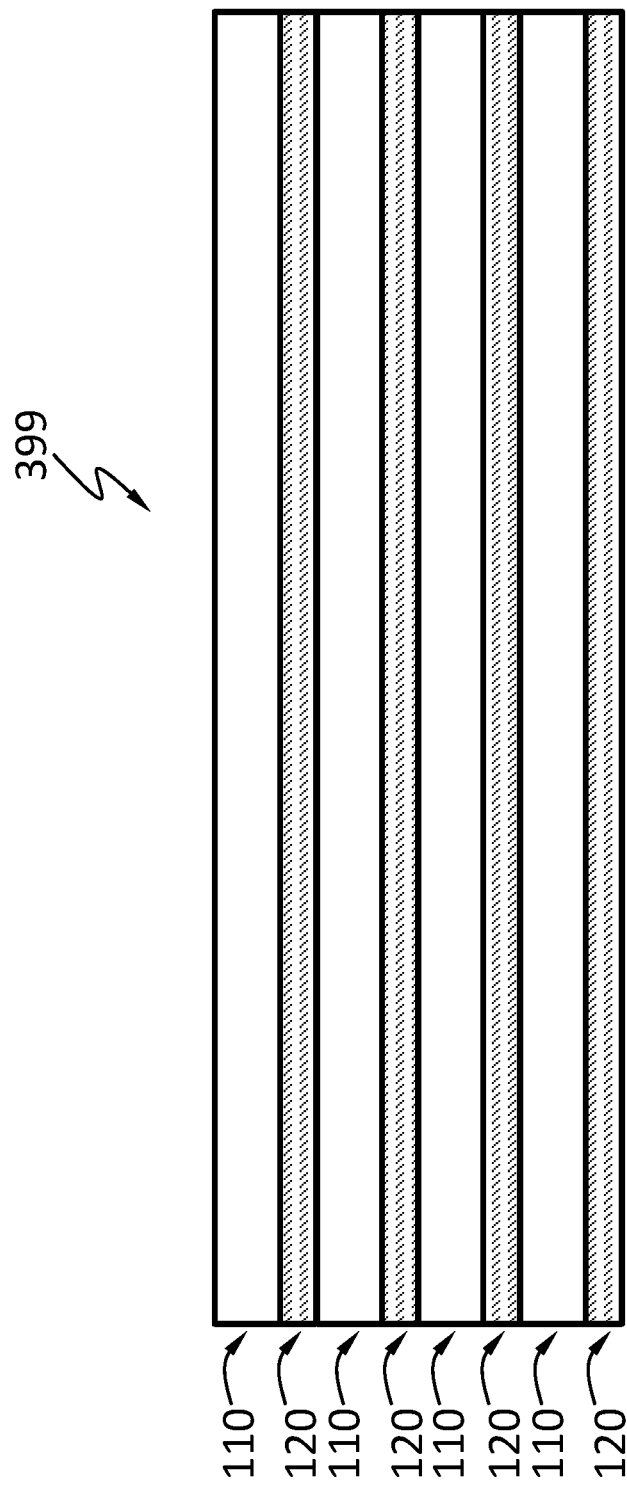
FIG. 3A shows that the electronics layer as shown in FIG. 2 allows stacking multiple X-ray detectors, according to an embodiment of the present teaching.

FIG. 3A shows that the electronics layer 120 as shown in FIG. 2 allows stacking multiple semiconductor X-ray detectors 100 to form a new X-ray detector 399. In each electronics layer 120, the transmission lines 127 in FIG. 3A can facilitate routing of signals of all pixels to a side of the wafer for readout. The signals can be gathered for X-ray detection. The electronics system 121 as described below may have low enough power consumption to eliminate bulky cooling mechanisms, which also helps to enable the stacked structure in FIG. 3A. The multiple semiconductor X-ray detectors 100 in the stack do not have to be identical. For example, the multiple semiconductor X-ray detectors 100 may differ in thickness, structure, or material.

Figure 3B:
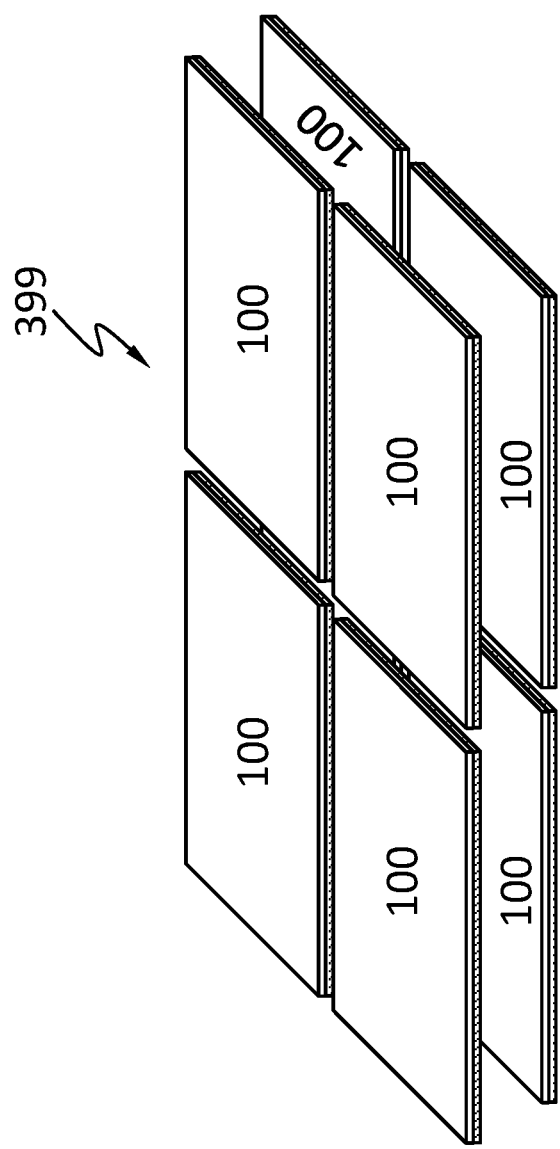
FIG. 3B schematically shows a top view of multiple stacked X-ray detectors, according to an embodiment of the present teaching.

FIG. 3B schematically shows a top view of multiple semiconductor X-ray detectors 100 stacked, according to an embodiment of the present teaching. Each layer may have multiple detectors 100 tiled to cover a larger area. The tiled detectors 100 in one layer can be staggered relative to the tiled detectors 100 in another layer, which may eliminate gaps in which incident X-ray photons cannot be detected.

Figure 3C:
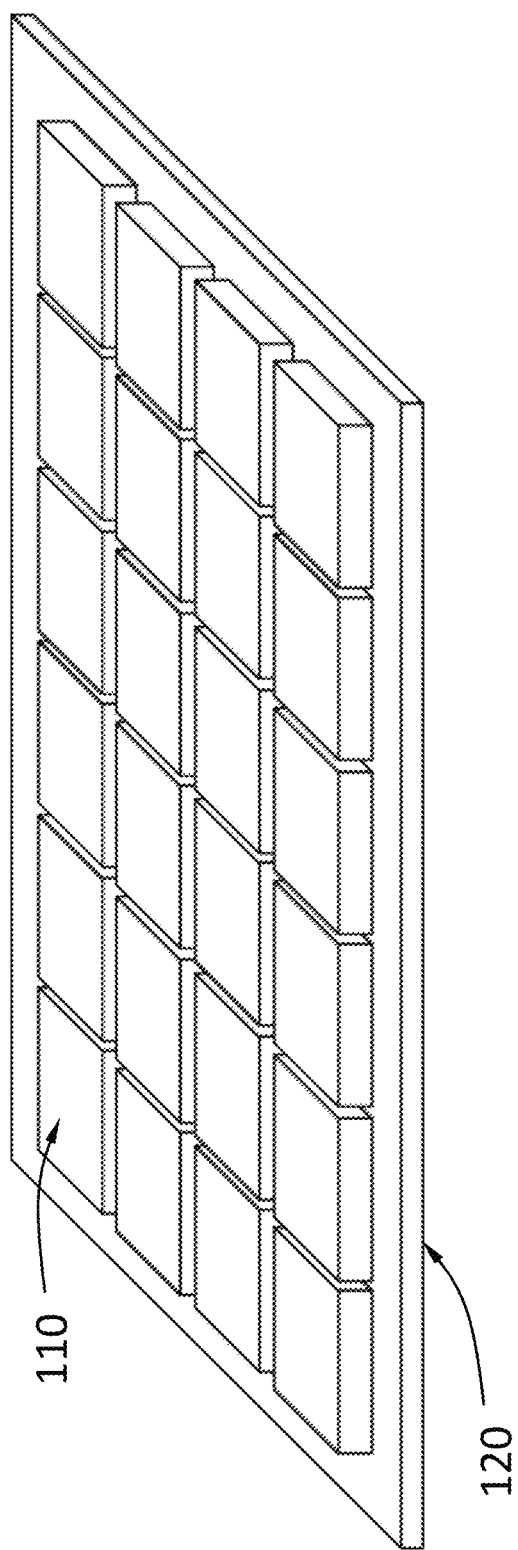
FIG. 3C schematically shows an example where the electronics layer is made on a single substrate and the X-ray absorption layer includes multiple chips bonded to the electronics layer.

The electronics layer 120, the X-ray absorption layer 110, or both may include multiple chips. For example, the electronics layer 120 may be made on a single substrate and the X-ray absorption layer 110 includes multiple chips bonded to the electronics layer 120, as FIG. 3C schematically shows.

Within an X-ray detector made entirely on the same substrate, the error of the location of a measured value of the characteristic is usually well controlled. For example, if the X-ray detector has multiple pixels arranged in an array, their relative locations to one another may be well defined by the fabrication process, e.g., by suitable alignment techniques in lithography. When one X-ray detector is stacked over another X-ray detector, after at least one of them is already fabricated, the relative positioning of the one X-ray detector with respect to the other is more difficult to control. When an X-ray detector includes multiple chips mounted to another layer, the relative positioning of the chips is also more difficult to control.

The misalignment of one X-ray detector relative to anther X-ray detector may be determined by imaging with one or both of the X-ray detectors.

Figure 4A:
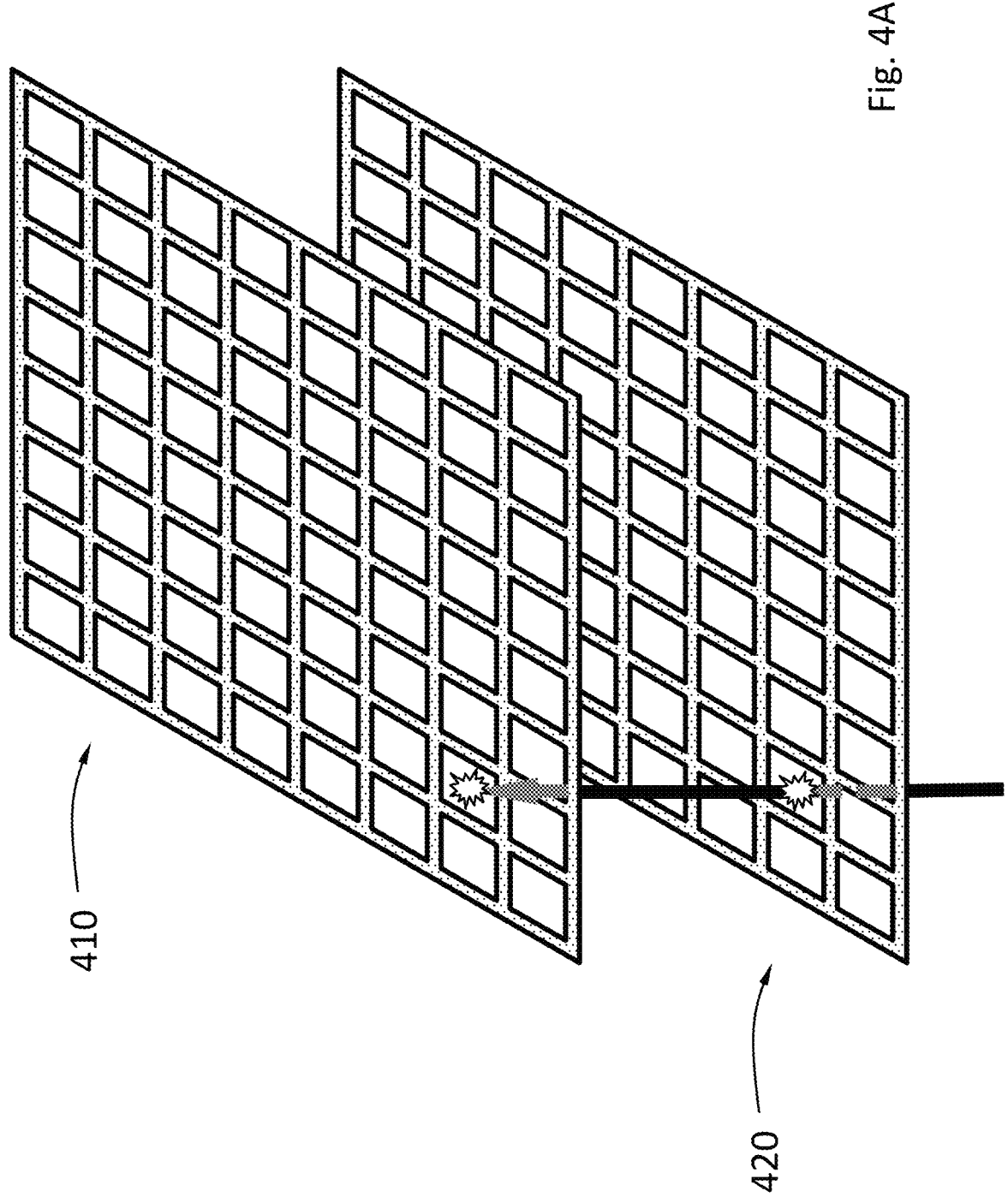
FIG. 4A schematically shows that two stacked X-ray detectors and are aligned.

FIG. 4A schematically shows that two stacked X-ray detectors 410 and 420 are aligned. Each of the detectors 410 and 420 may have multiple pixels. Within each of the detectors 410 and 420, the positions of the pixels relative to one another may be known. When a beam of X-ray is directed to the detector 410, a part of the beam of X-ray is absorbed and detected by the detector 410 and another part of the beam of X-ray passes through the detector 410 and is detected by the detector 420.

FIG. 4B schematically shows images 410A and 420A the detectors 410 and 420 respectively should capture from the beam of X-ray if the detectors 410 and 420 are aligned.

Figure 4C:
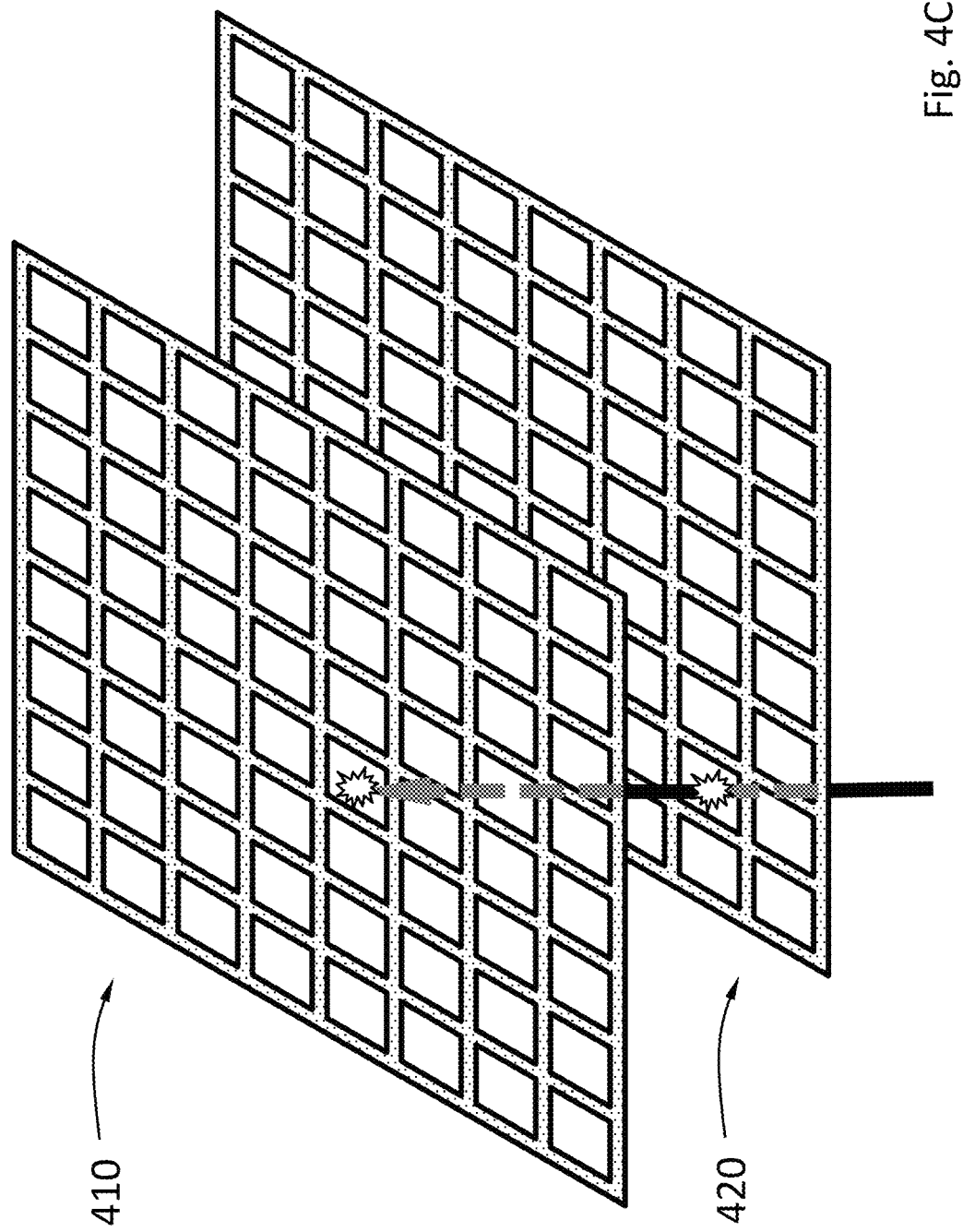
FIG. 4C schematically shows that the two X-ray detectors of FIG. 4A are misaligned.
Figure 4D:
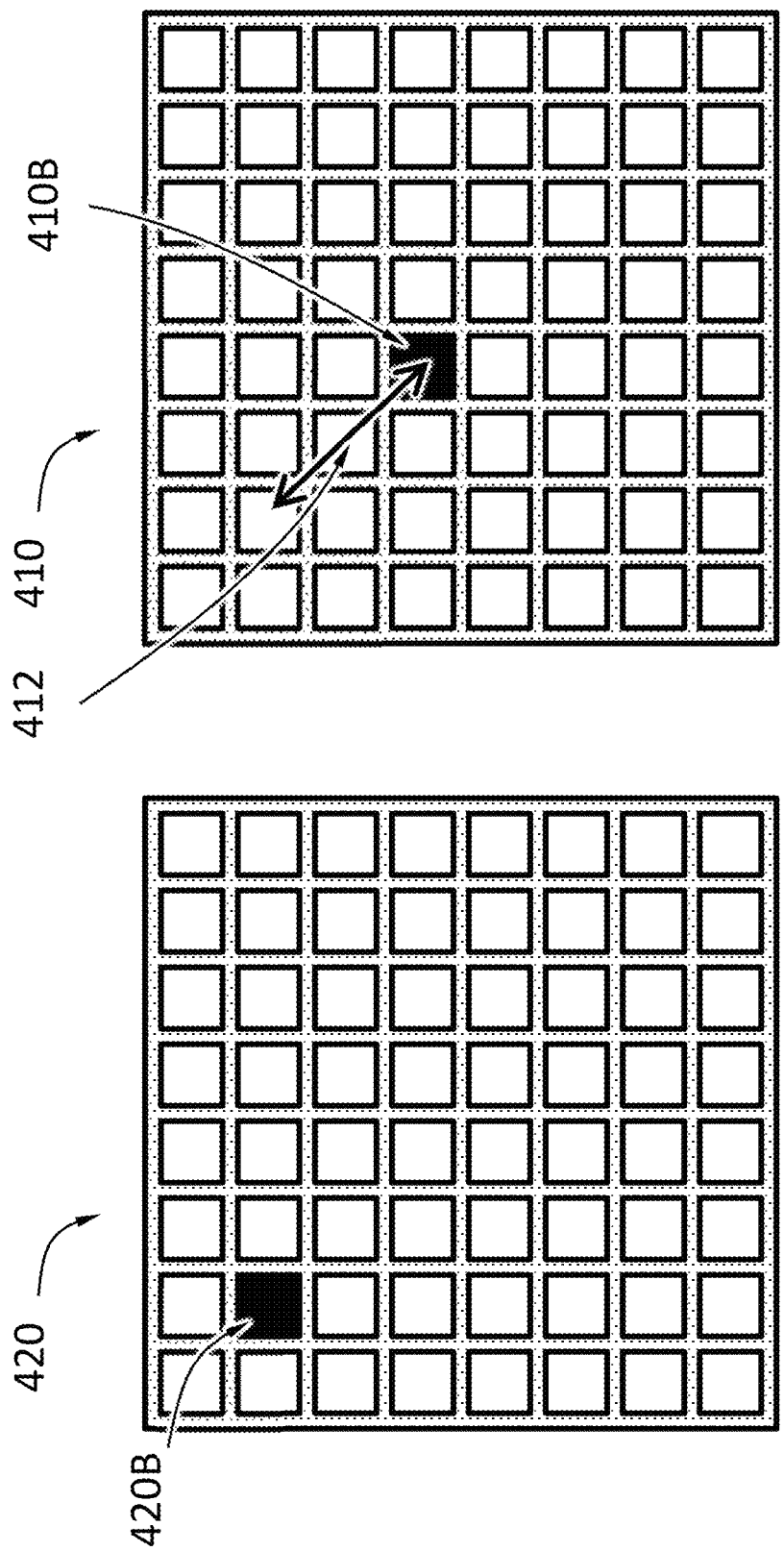
FIG. 4D schematically shows images the X-ray detectors of FIG. 4A capture when the detectors are misaligned.

FIG. 4C schematically shows that the detectors 410 and 420 are misaligned and FIG. 4D schematically shows images 410B and 420B the detectors 410 and 420 respectively capture from the beam of X-ray when the detectors 410 and 420 are misaligned. The misalignment of the detectors 410 and 420 with respect to each other can be obtained from the shift (e.g., as marked by arrow 412) between the images 410A and 410B, the shift between the images 420A and 420B, or both.

Figure 5A:
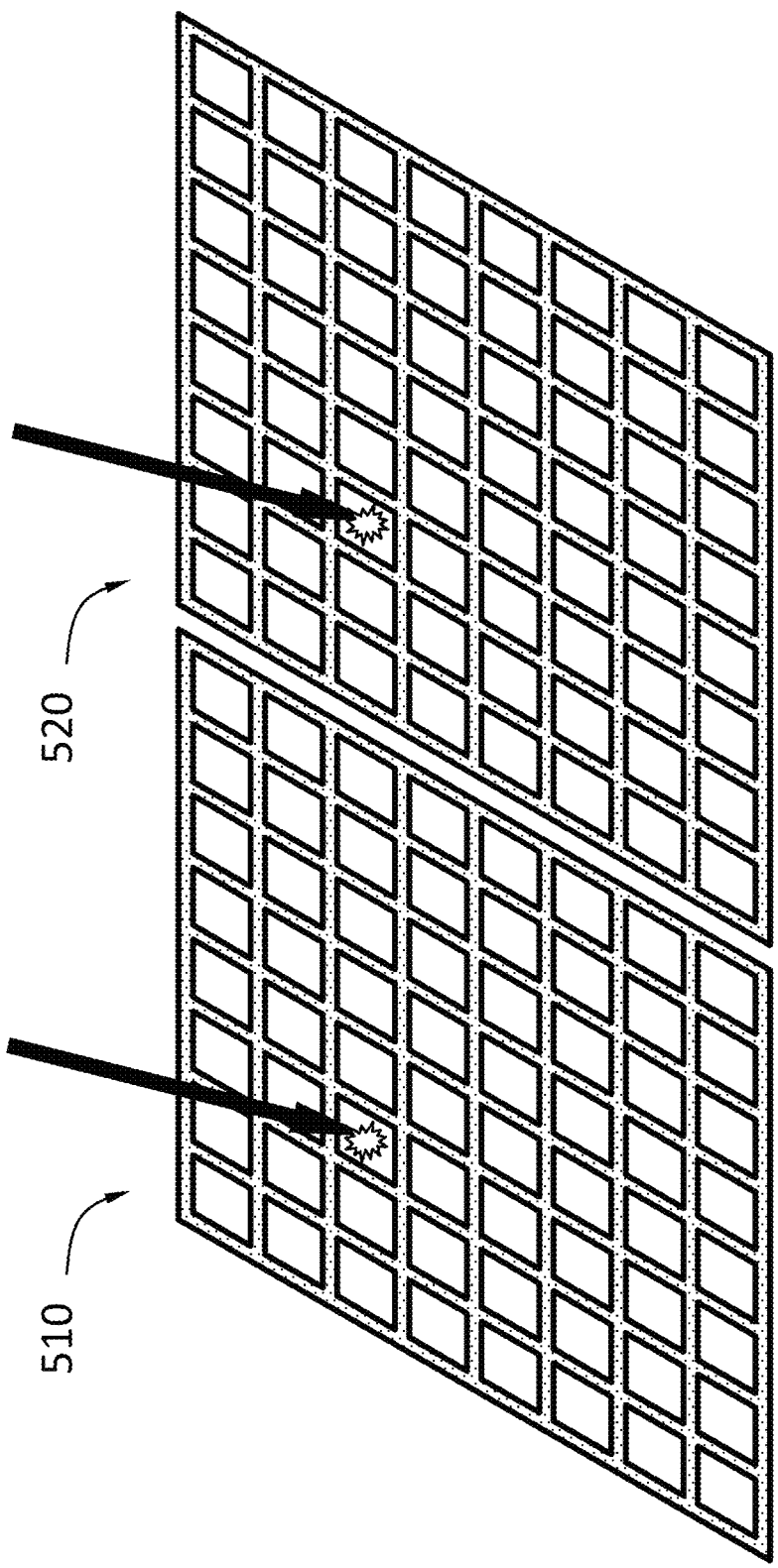
FIG. 5A schematically shows two X-ray detectors and arranged side by side are aligned.

FIG. 5A schematically shows two X-ray detectors 510 and 520 arranged side by side are aligned. Each of the detectors 510 and 520 may have multiple pixels. Within each of the detectors 510 and 520, the positions of the pixels relative to one another may be known. When two beams of X-ray are directed the detectors 510 and 520 respectively, or one beam of X-ray is directed to the detectors 510 and 520 at different time, the detectors 510 and 520 each capture an image of the beam directed thereto.

Figure 5B:
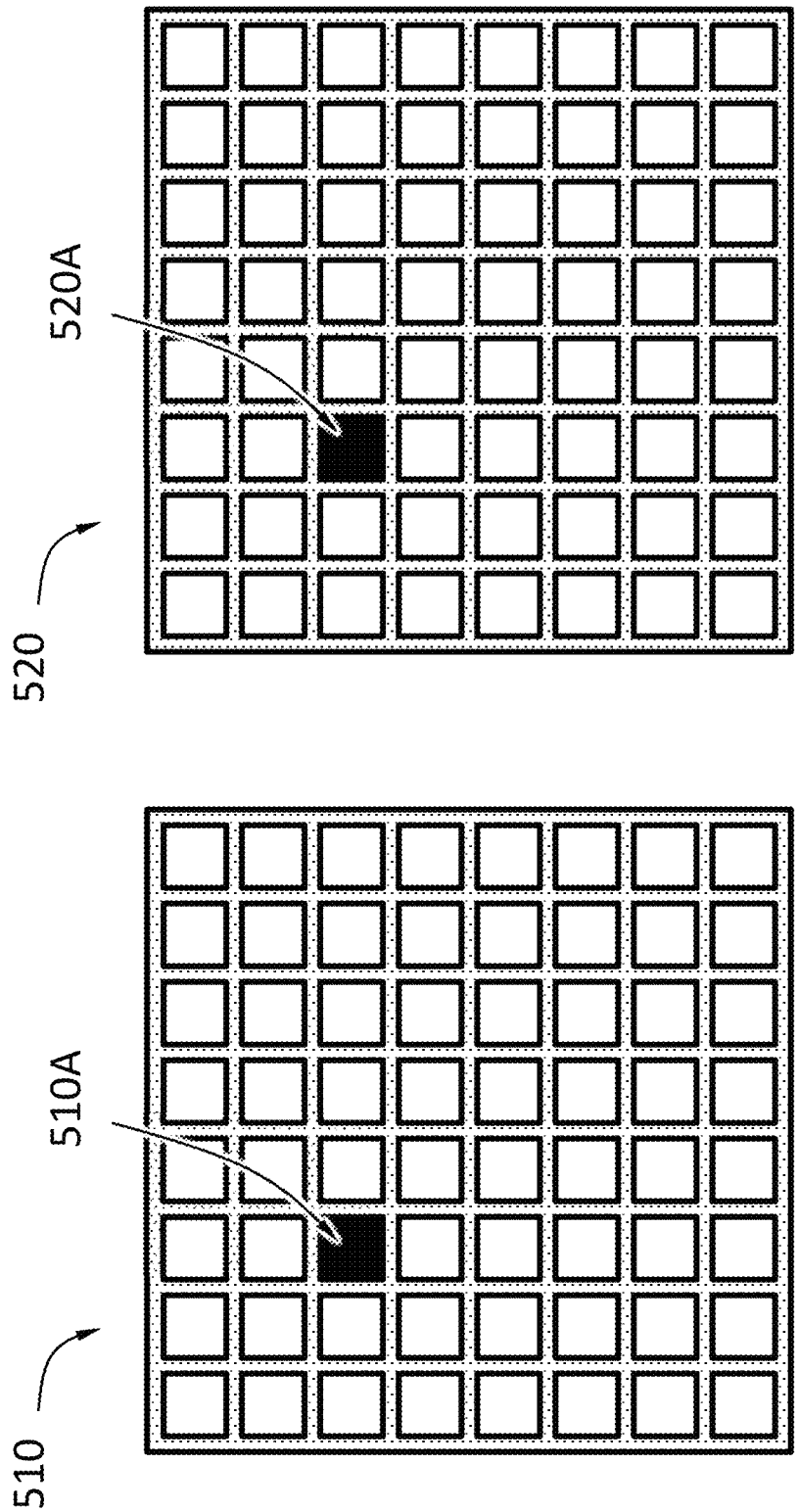
FIG. 5B schematically shows images the X-ray detectors of FIG. 5A should capture if the detectors are aligned.

FIG. 5B schematically shows images 510A and 520A the detectors 510 and 520 respectively should capture from the beam of X-ray if the detectors 510 and 520 are aligned.

Figure 5C:
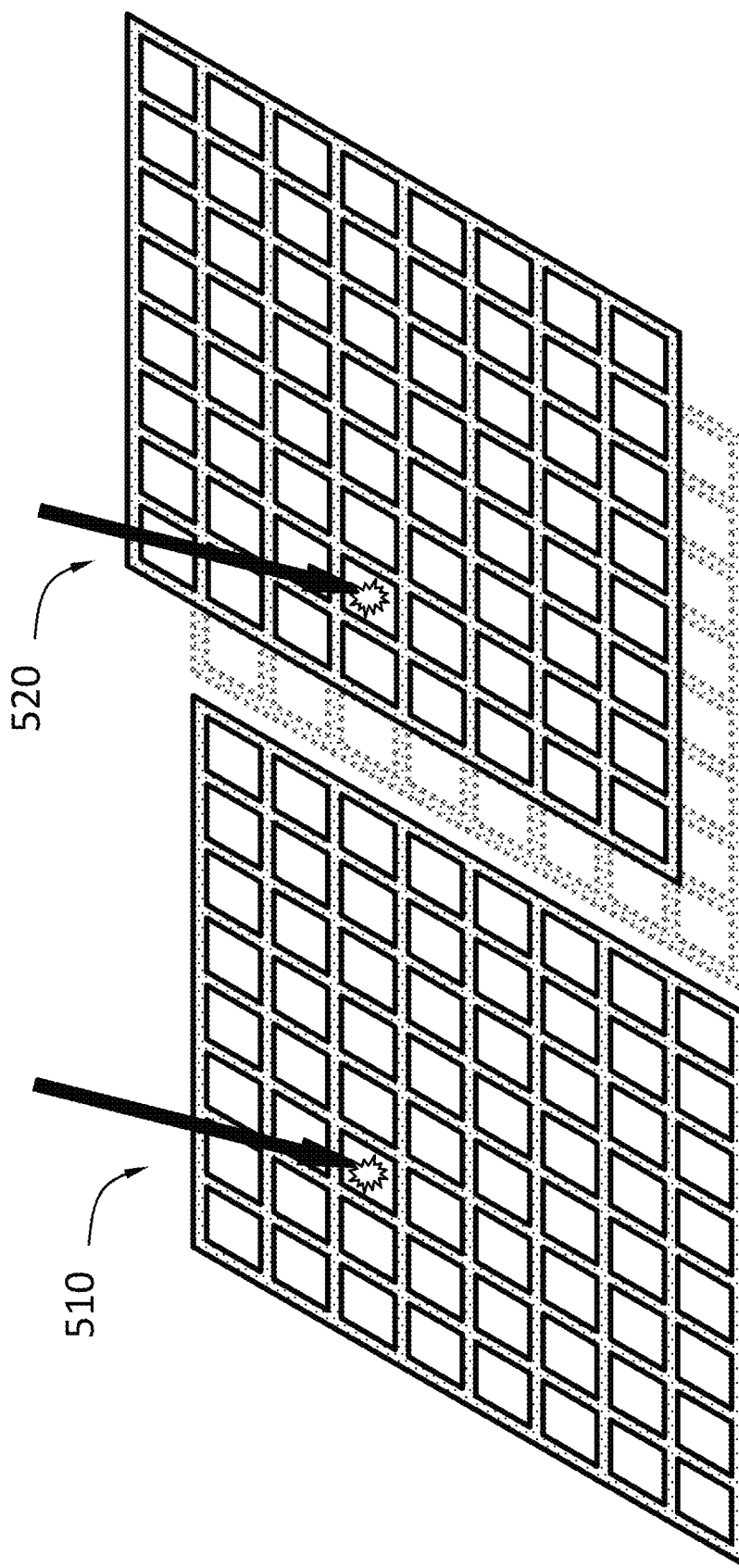
FIG. 5C schematically shows that the two X-ray detectors of FIG. 5A are misaligned.
Figure 5D:
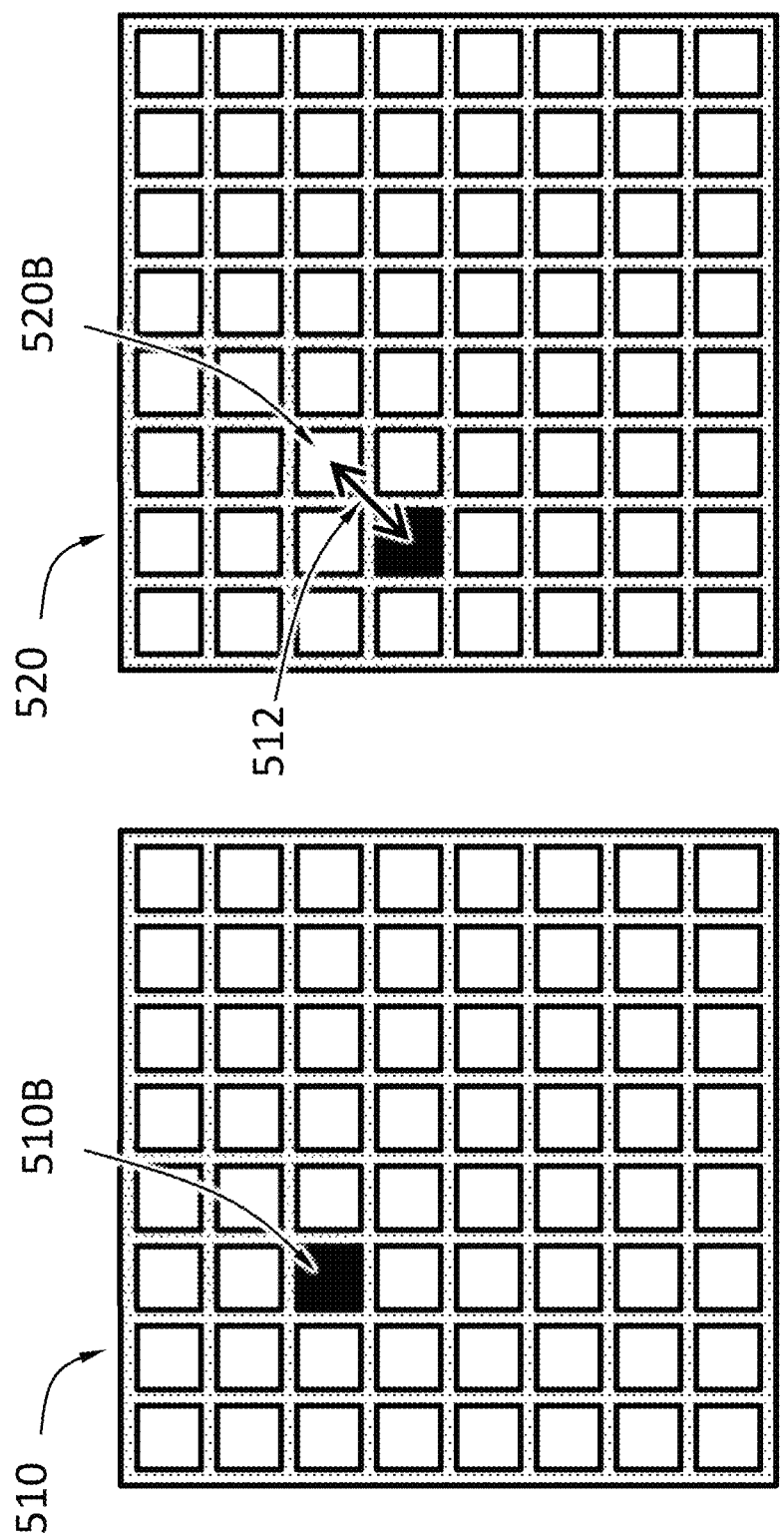
FIG. 5D schematically shows images the X-ray detectors of FIG. 5A capture when the X-ray detectors are misaligned.

FIG. 5C schematically shows that the detectors 510 and 520 are misaligned and FIG. 5D schematically shows images 510B and 520B the detectors 510 and 520 respectively capture from the beams of X-ray when the detectors 510 and 520 are misaligned. The misalignment of the detectors 510 and 520 with respect to each other can be obtained from the shift (e.g., as marked by arrow 512) between the images 520A and 520B, the shift between the images 510A and 510B, or both.

FIG. 6A schematically shows that two stacked X-ray detectors 610 and 620 are aligned. Each of the detectors 610 and 620 may have multiple pixels. Within each of the detectors 610 and 620, the positions of the pixels relative to one another may be known. An image of a scene 650 of X-ray is captured by each of the detectors 610 and 620.

Figure 6B:
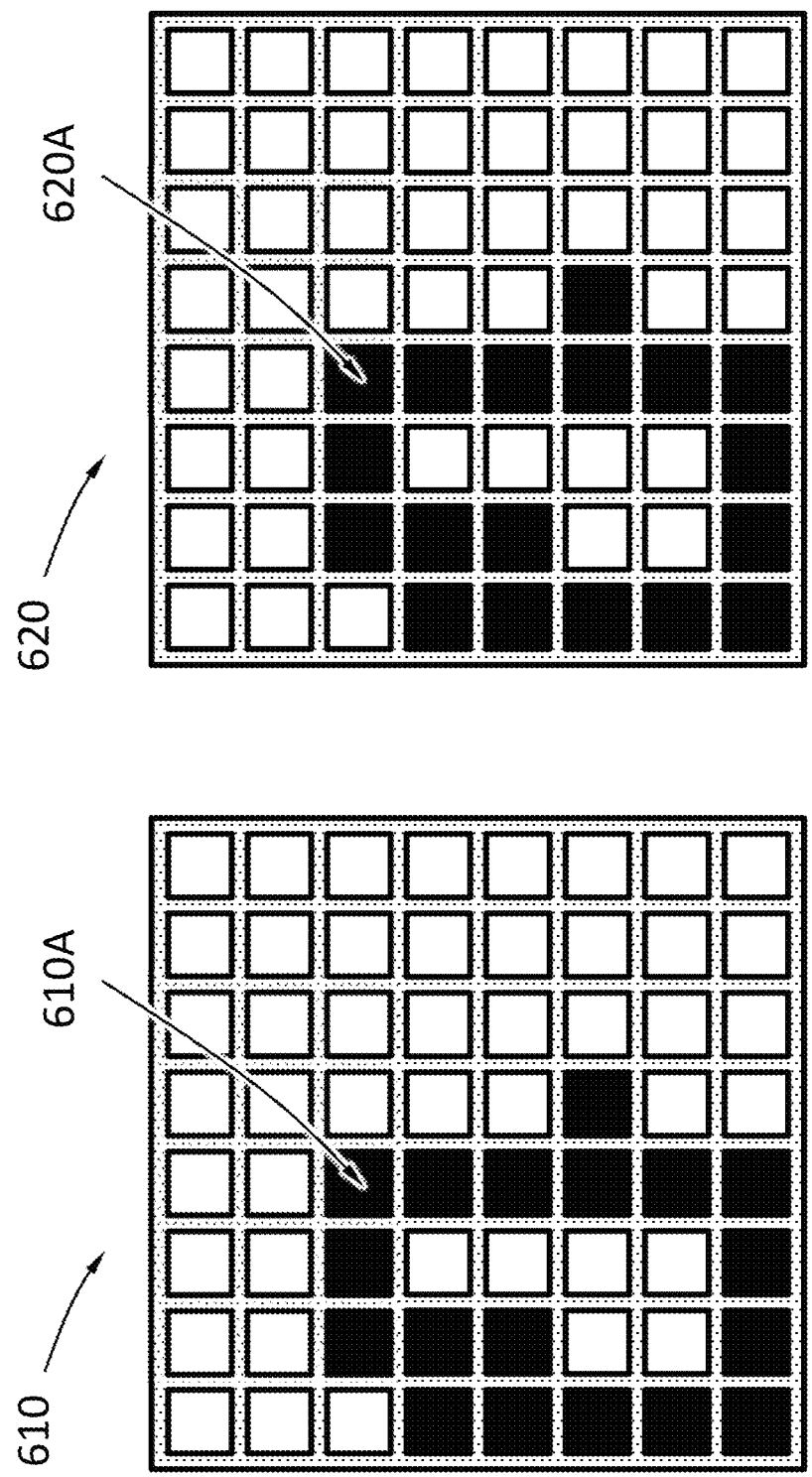
FIG. 6B schematically shows images the X-ray detectors of FIG. 6A should capture if the X-ray detectors are aligned.

FIG. 6B schematically shows images 610A and 620A the detectors 610 and 620 respectively should capture from the scene 650 if the detectors 610 and 620 are aligned.

Figure 6C:
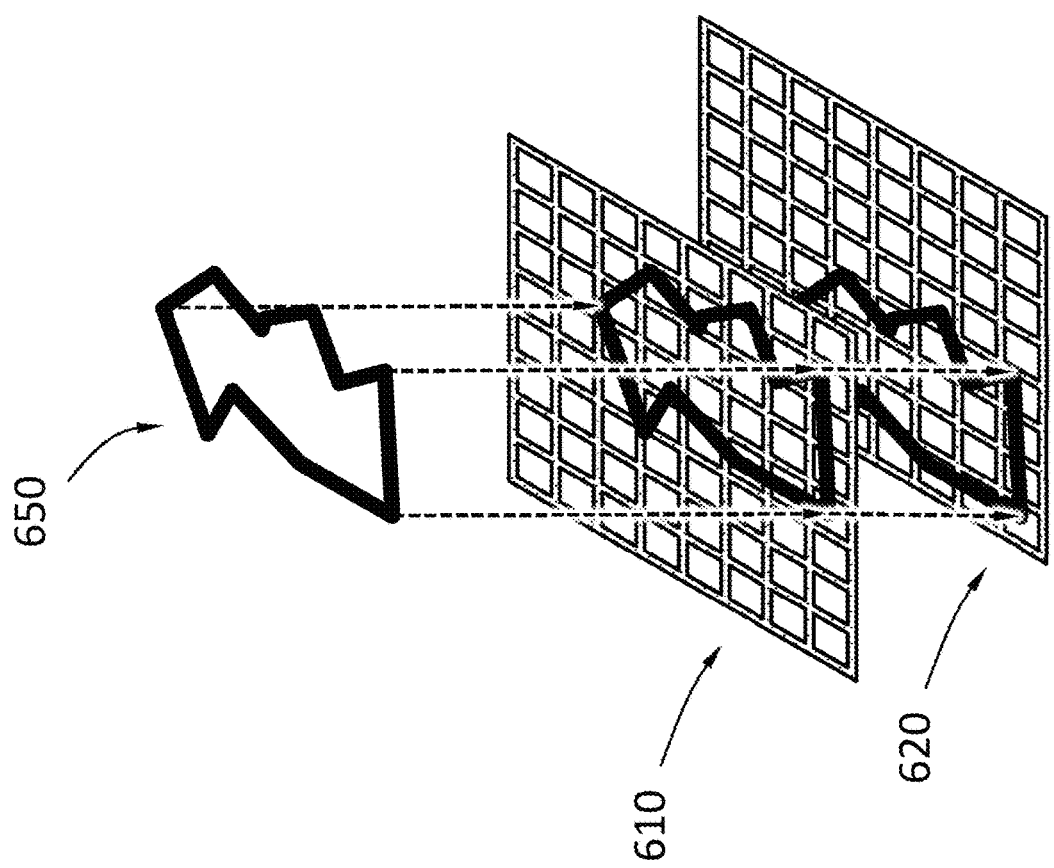
FIG. 6C schematically shows that the two X-ray detectors of FIG. 6A are misaligned.
Figure 6D:
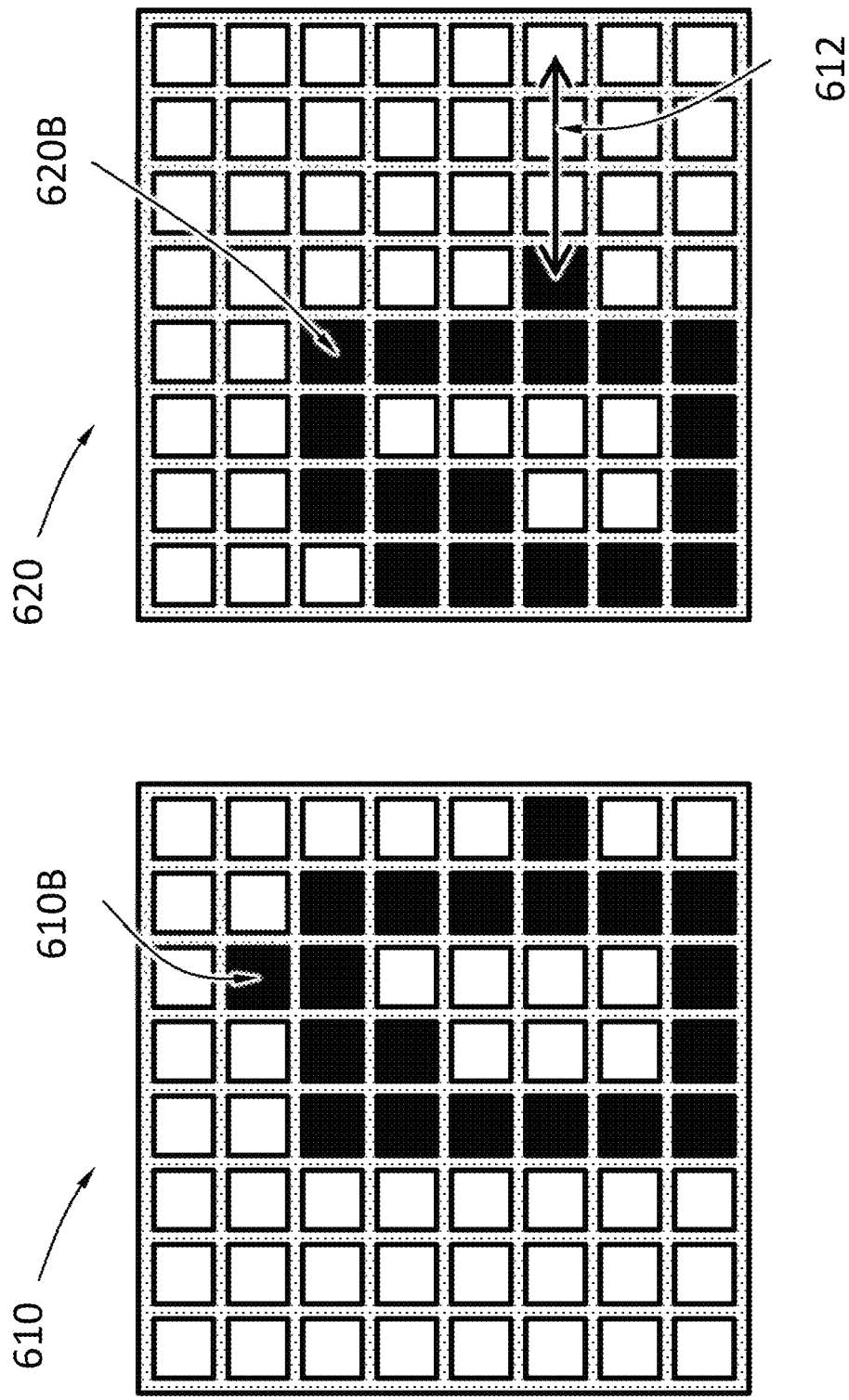
FIG. 6D schematically shows images the X-ray detectors of FIG. 4A capture when the X-ray detectors are misaligned.

FIG. 6C schematically shows that the detectors 610 and 620 are misaligned and FIG. 6D schematically shows images 610B and 620B the detectors 610 and 620 respectively capture from the scene 650 when the detectors 610 and 620 are misaligned. The misalignment of the detectors 610 and 620 with respect to each other can be obtained from the shift (e.g., as marked by arrow 612) between the images 620A and 620B, the shift between the images 610A and 610B, or both.

Figure 7A:
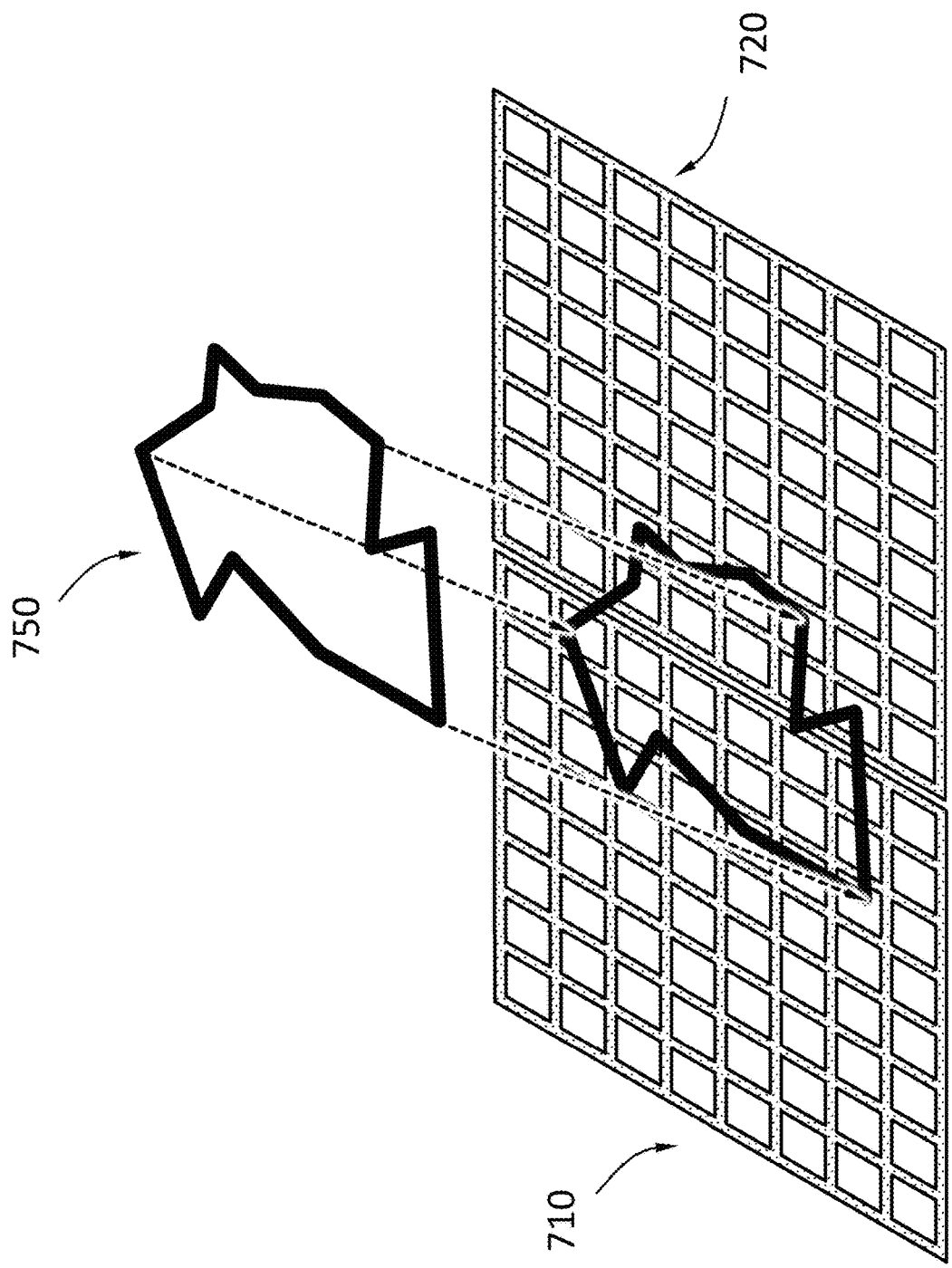
FIG. 7A schematically shows two X-ray detectors and arranged side by side are aligned.

FIG. 7A schematically shows that two X-ray detectors 710 and 720 arranged side by side are aligned. Each of the detectors 710 and 720 may have multiple pixels. Within each of the detectors 710 and 720, the positions of the pixels relative to one another may be known. An image of a part of a scene 750 of X-ray is captured by the detector 710 and an image of another part of the scene 750 is captured by the detector 720.

Figure 7B:
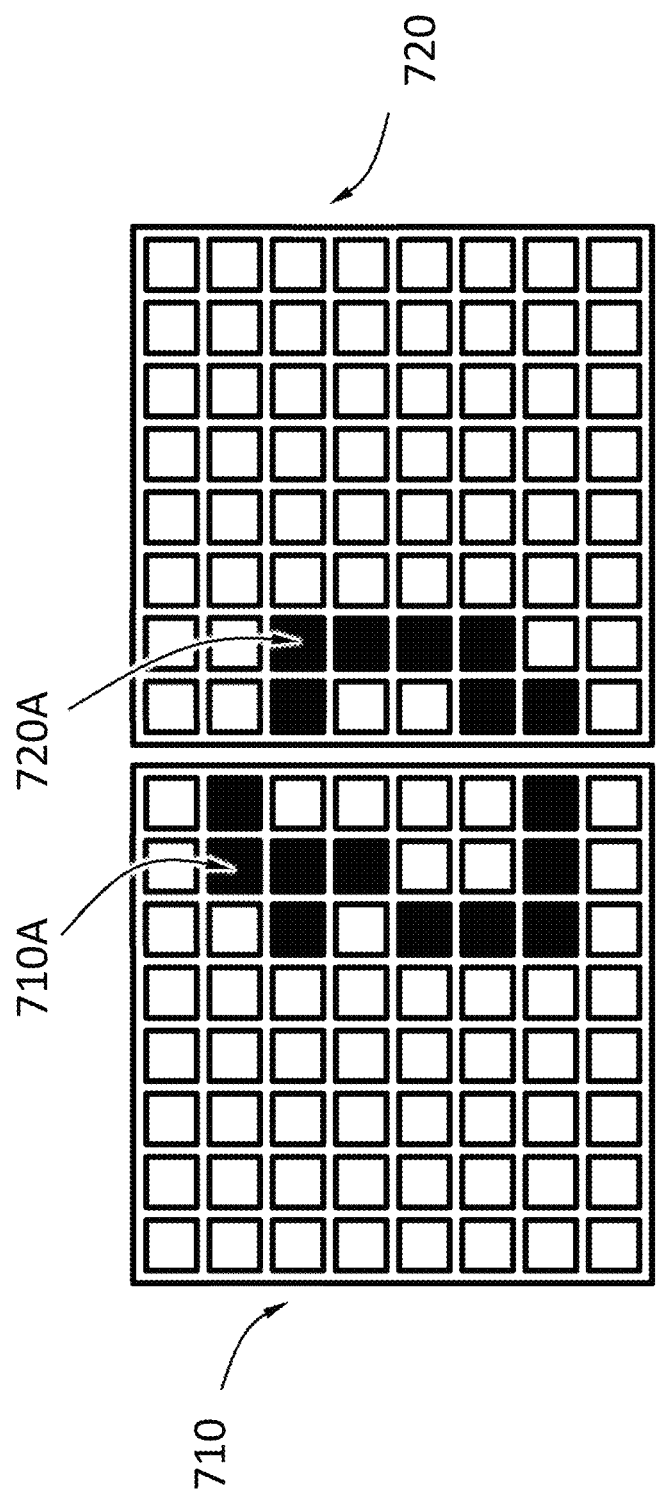
FIG. 7B schematically shows images the X-ray detectors of FIG. 7A should capture if the X-ray detectors are aligned.

FIG. 7B schematically shows images 710A and 720A the detectors 710 and 720 respectively should capture from the scene 750 if the detectors 710 and 720 are aligned.

Figure 7C:
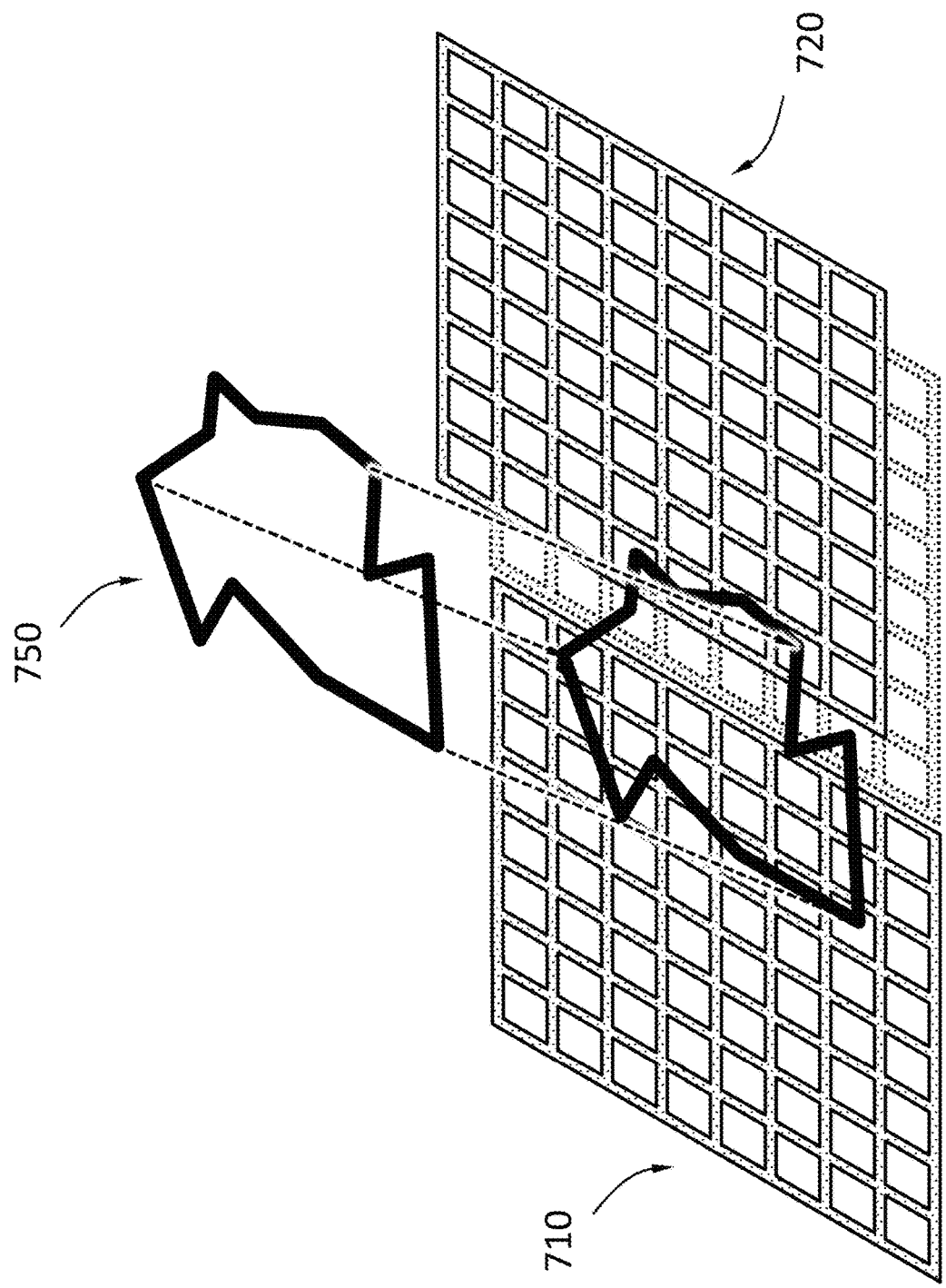
FIG. 7C schematically shows that the two X-ray detectors of FIG. 7A are misaligned.
Figure 7D:
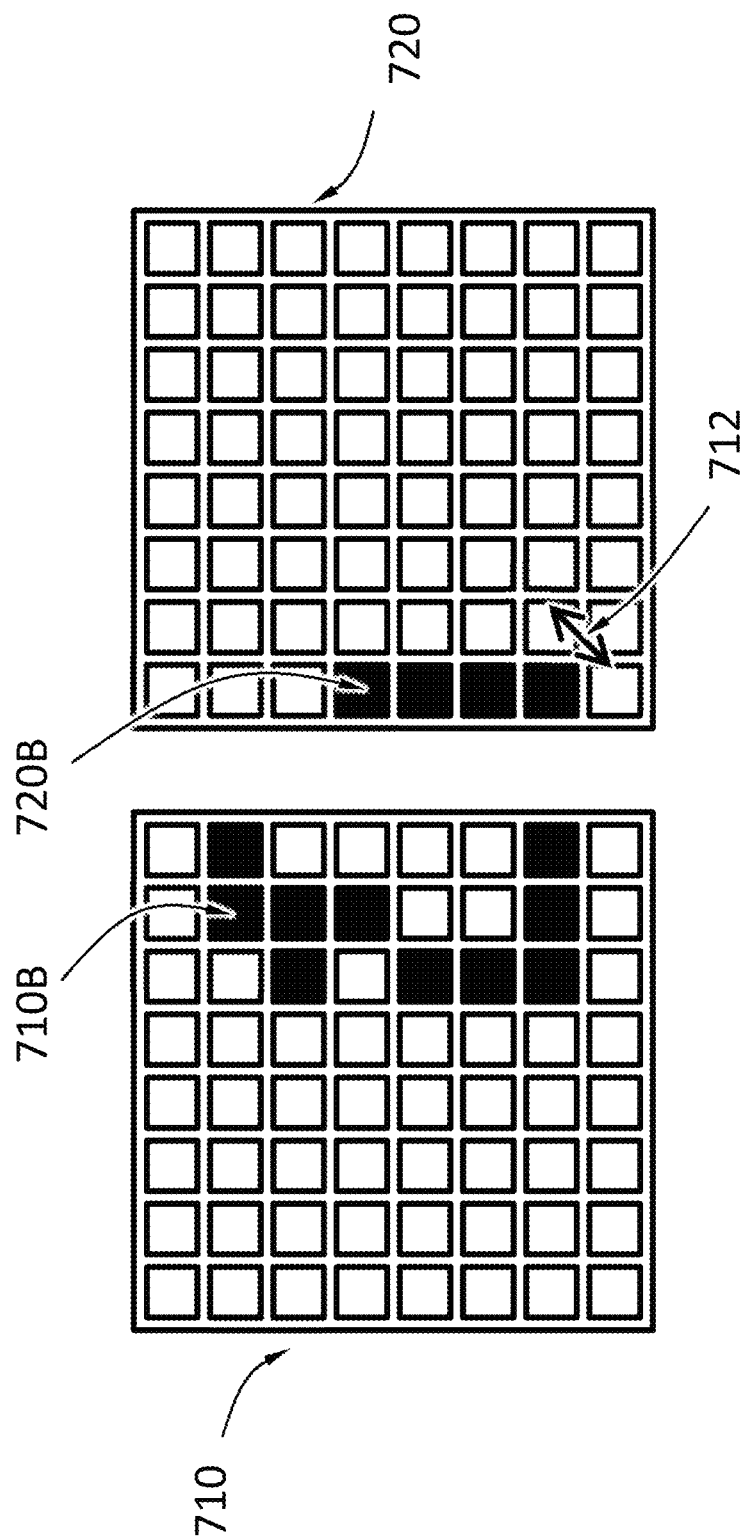
FIG. 7D schematically shows images the X-ray detectors of FIG. 7A capture when the X-ray detectors are misaligned.

FIG. 7C schematically shows that the detectors 710 and 720 are misaligned and FIG. 7D schematically shows images 710B and 720B the detectors 710 and 720 respectively capture from the scene 750 when the detectors 710 and 720 are misaligned. The misalignment of the detectors 710 and 720 with respect to each other can be obtained from the shift (e.g., as marked by arrow 712) between the images 720A and 720B, the shift between the images 710A and 710B, or both.

Figure 8A:
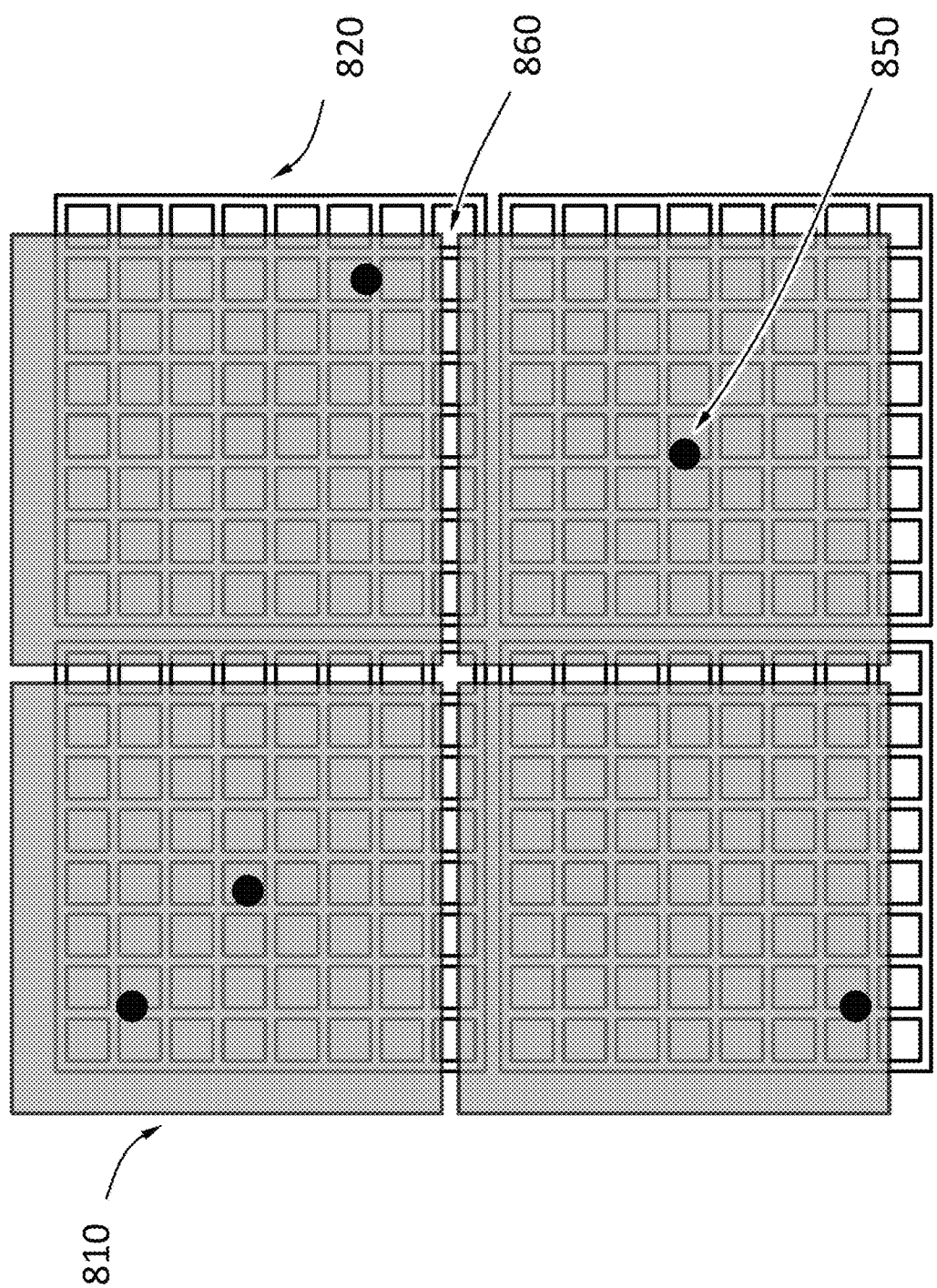
FIG. 8A schematically shows that two stacked X-ray detectors and are aligned.

FIG. 8A schematically shows that two stacked X-ray detectors 810 and 820 are aligned. Each of the detectors 810 and 820 may have multiple pixels. Within each of the detectors 810 and 820, the positions of the pixels relative to one another may be known. When X-ray with essentially uniform intensity across the surface of the detector 810 is directed to the detectors 810 and 820, part of the X-ray may be absorbed by the detector 810 and another part may be absorbed by the detector 820. Because the absorption of the X-ray by the detector 810 may not be spatially uniform, for example, due to structures of the detector 810 such as gaps 860 between pixels and solder bumps 850, the detector 820 captures an image of these structures of the detector 810.

Figure 8B:
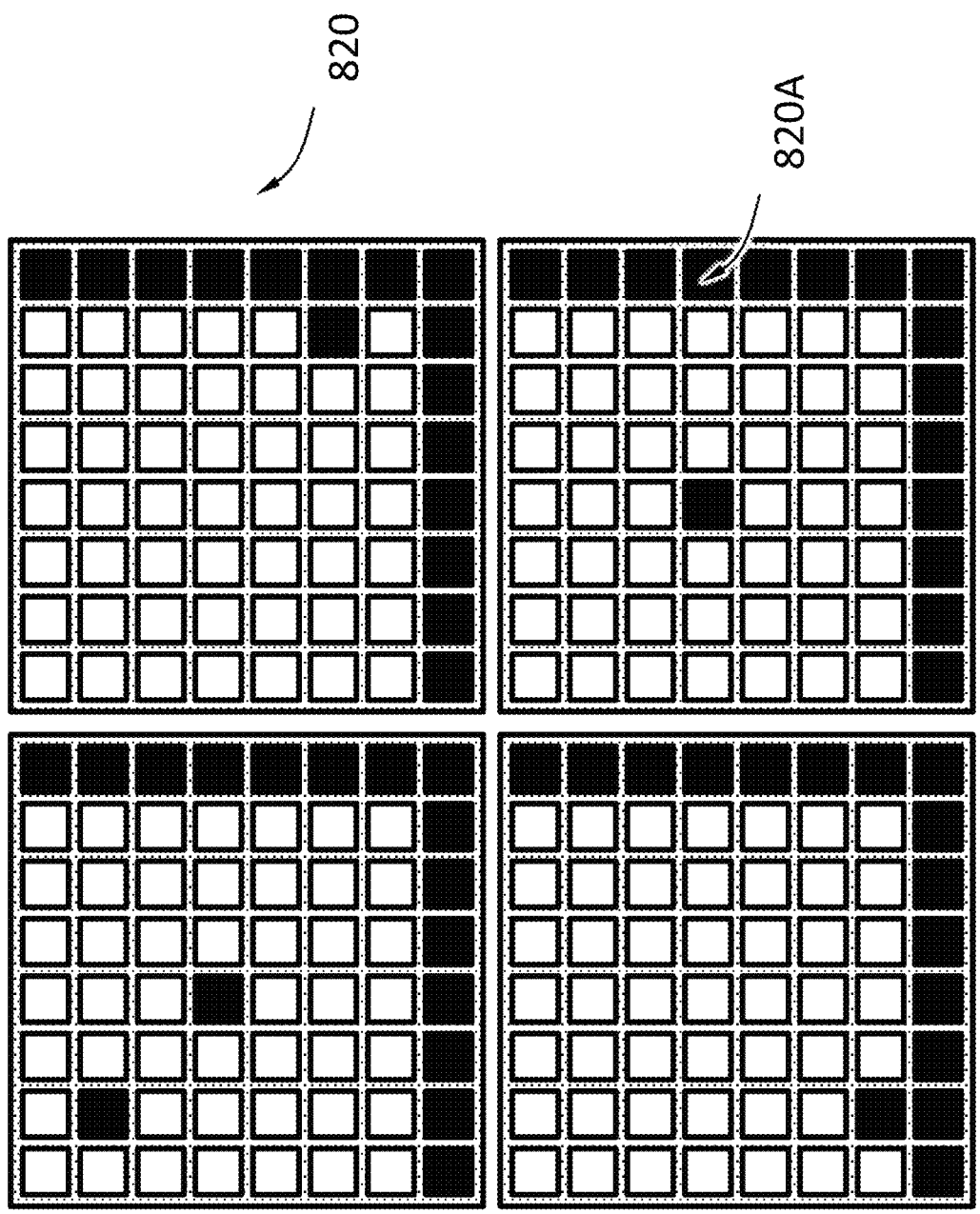
FIG. 8B schematically shows an image of structures of one of the X-ray detectors the other X-ray detector should capture, if the X-ray detectors of FIG. 8A are aligned.

FIG. 8B schematically shows an image 820A of the structures of the detector 810 the detector 820 should capture, if the detectors 810 and 820 are aligned.

Figure 8C:
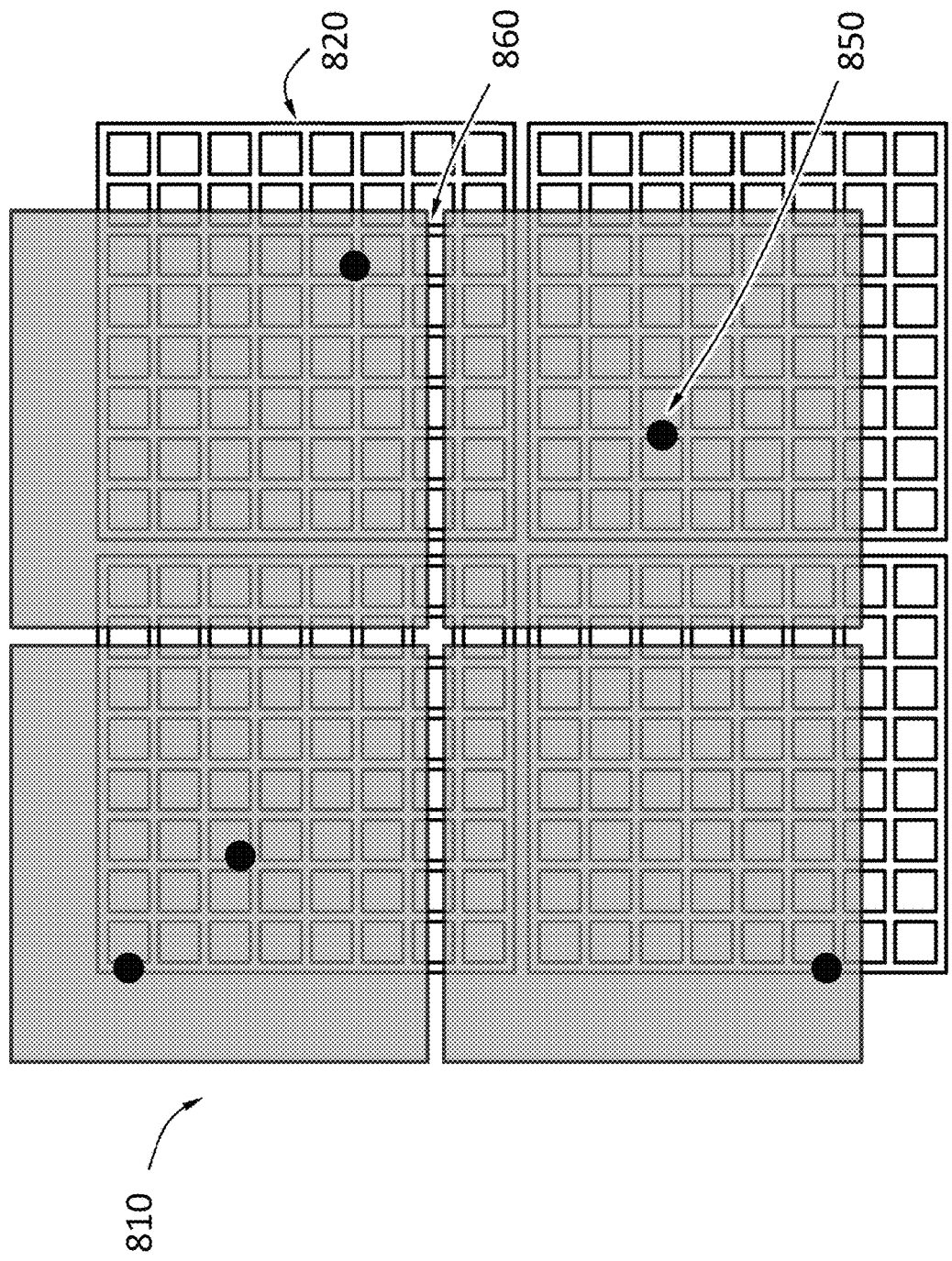
FIG. 8C schematically shows that the two X-ray detectors of FIG. 8A are misaligned.
Figure 8D:
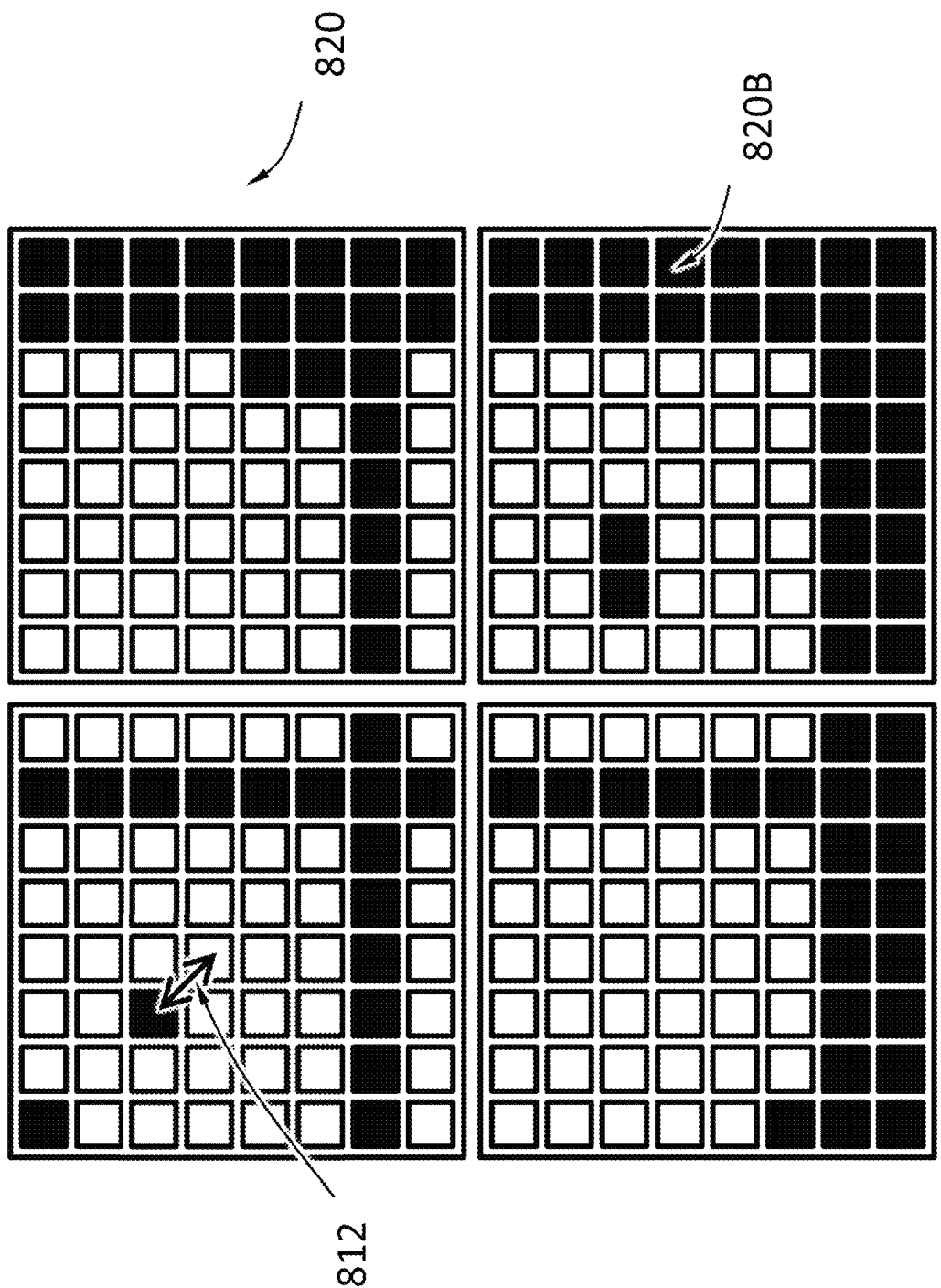
FIG. 8D schematically shows an image of structures of one of the X-ray detectors captured by the other X-ray detector, when the X-ray detectors of FIG. 8A are misaligned.

FIG. 8C schematically shows that the detectors 810 and 820 are misaligned and FIG. 8D schematically shows the image 820B of the structures of the detector 810 captured by the detector 820 when the detectors 810 and 820 are misaligned. The misalignment of the detectors 810 and 820 with respect to each other can be obtained from the shift (e.g., as marked by arrow 812) between the images 820A and 820B.

Figure 9:
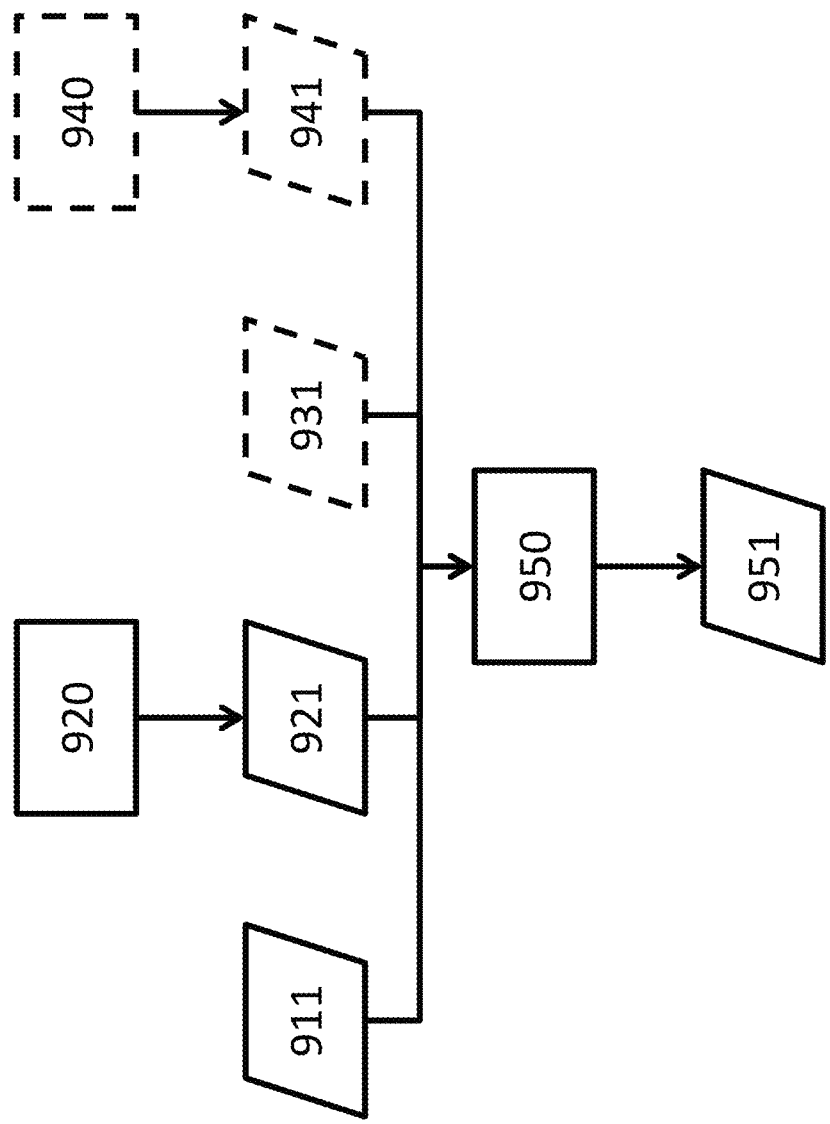
FIG. 9 schematically shows a flow chart for determining misalignment of a first X-ray detector and a second X-ray detector with respect to one another.

FIG. 9 schematically shows a flow chart for determining misalignment of a first X-ray detector and a second X-ray detector with respect to one another. In procedure 920, an image 921 from the first detector is obtained when the first detector and the second detector are misaligned. Optionally in procedure 940, an image 941 from the second detector is obtained when the first detector and the second detector are misaligned. In procedure 950, a misalignment 951 between the first detector and the second detector when the first and second detectors are misaligned is determined based on a shift between the image 921 and an image 911 the first detector should capture if the first detector and the second detector are aligned, and optionally a shift between the image 941 and an image 931 the second detector should capture if the first detector and the second detector are aligned.

The X-ray detectors depicted in FIGS. 4A-8D and referred to in FIG. 9 may be the X-ray detector 100 illustrated in FIG. 1A, FIG. 1B or FIG. 1C.

An X-ray detector may have multiple chips and the positioning of the chips may have errors and may not be perfectly aligned to one another. Not all chips overlap one another. Misalignment of two chips may be determined from a chain of chips where each link comprises a pair of overlapping chips. As shown in FIG. 10, two X-ray detector 1010 and 1020 are stacked on each other. The X-ray detector 1010 has multiple chips such as 1010A, 1010B, 1010C and 1010D; the X-ray detector 1020 has multiple chips such as 1020A, 1020B, 1020C and 1020D. The chips 1010D and 1020C do not overlap. However, the misalignment of the chips 1010D and 1020C may be determined from the misalignment of chips 1010D and 1020A, the misalignment of the chips 1020A and 1010B, the misalignment of the chips 1010B and 1020B, the misalignment of the chips 1020B and 1010C, and the misalignment of the chips 1010C and 1020C.

Figure 11B:
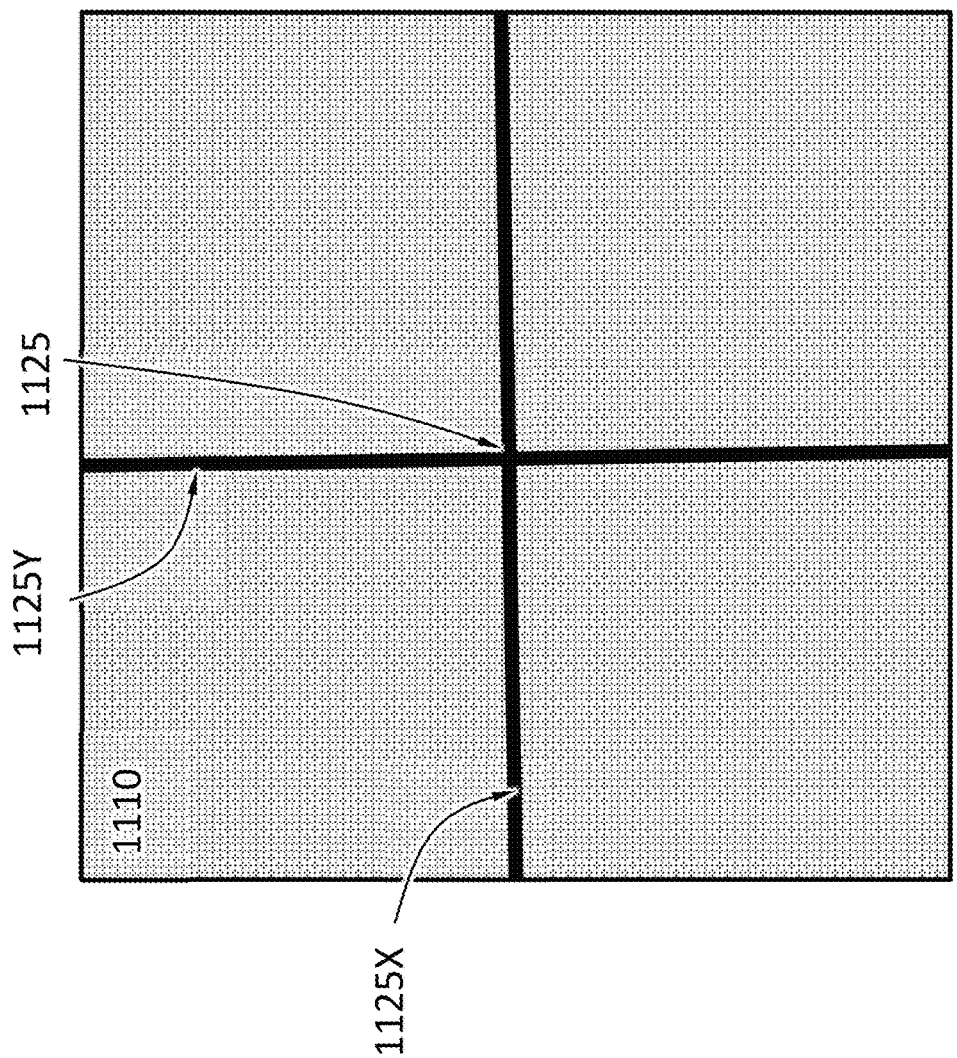
FIG. 11B schematically shows the relative position of a cross pattern and a chip.

FIG. 11A schematically shows that misalignment of chips 1110 of an X-ray detector with respect to one another may be determined using a scene 1120 with multiple cross patterns 1125. The relative positions of the cross patterns with respect to one other are known. The chips 1110 are positioned such that each chip captures an image of at least one of the cross patterns, despite that the chips 1110 are not perfectly aligned with respect to one another. FIG. 11B schematically shows the relative position of a cross pattern 1125 and a chip 1110. The chip 1110 may be shifted or rotated relative to the cross pattern 1125. The cross pattern 1125 may include two lines 1125X and 1125Y that have a finite width and are perpendicular to each other.

Figure 11C:
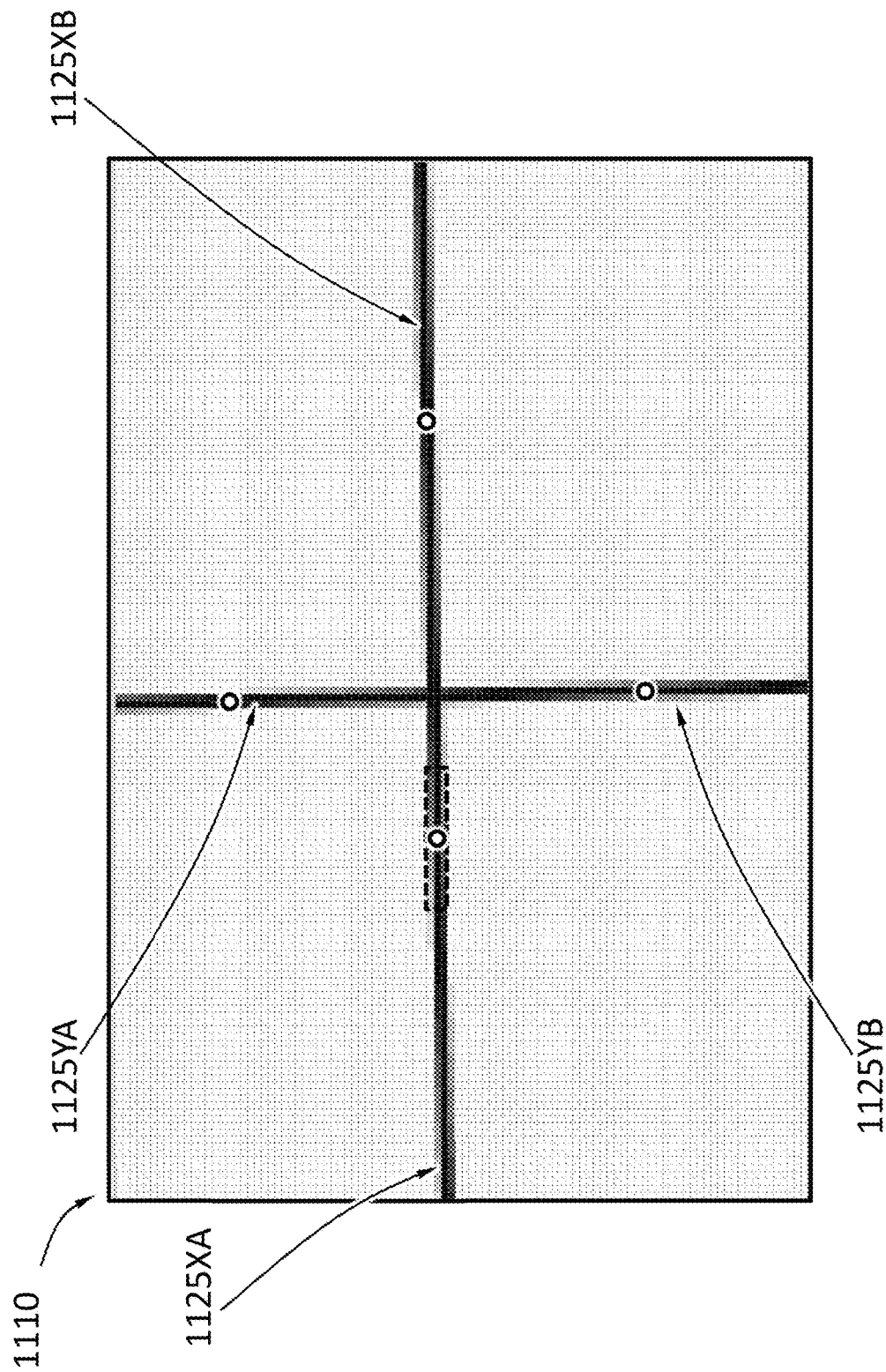
FIG. 11C schematically shows an image of the cross pattern captured by the chip.

FIG. 11C schematically shows an image of the cross pattern 1125 captured by the chip 1110. The image includes four parts 1125XA, 1125XB, 1125YA and 1125YB. The parts 1125XA and 1125XB belong to the image of the line 1125X. The parts 1125XA and 1125XB are on opposite sides of the cross point. The parts 1125YA and 1125YB belong to the image of the line 1125Y. The parts 1125YA and 1125YB are on opposite sides of the cross point. The positions of the lines 1125X and 1125Y, and thus the cross pattern 1125 relative to the chip 1110 may be determined from the four parts 1125XA, 1125XB, 1125YA and 1125YB.

Figure 11D:
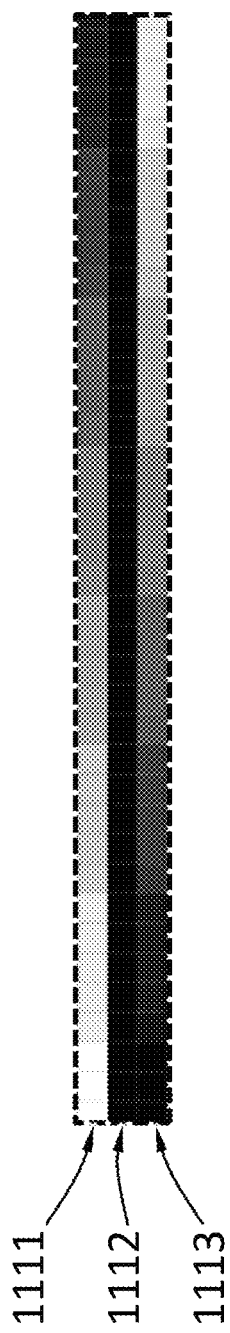
FIG. 11D shows a portion (marked by the dotted box in FIG. 11C) of a part of the image.
Figure 11E:
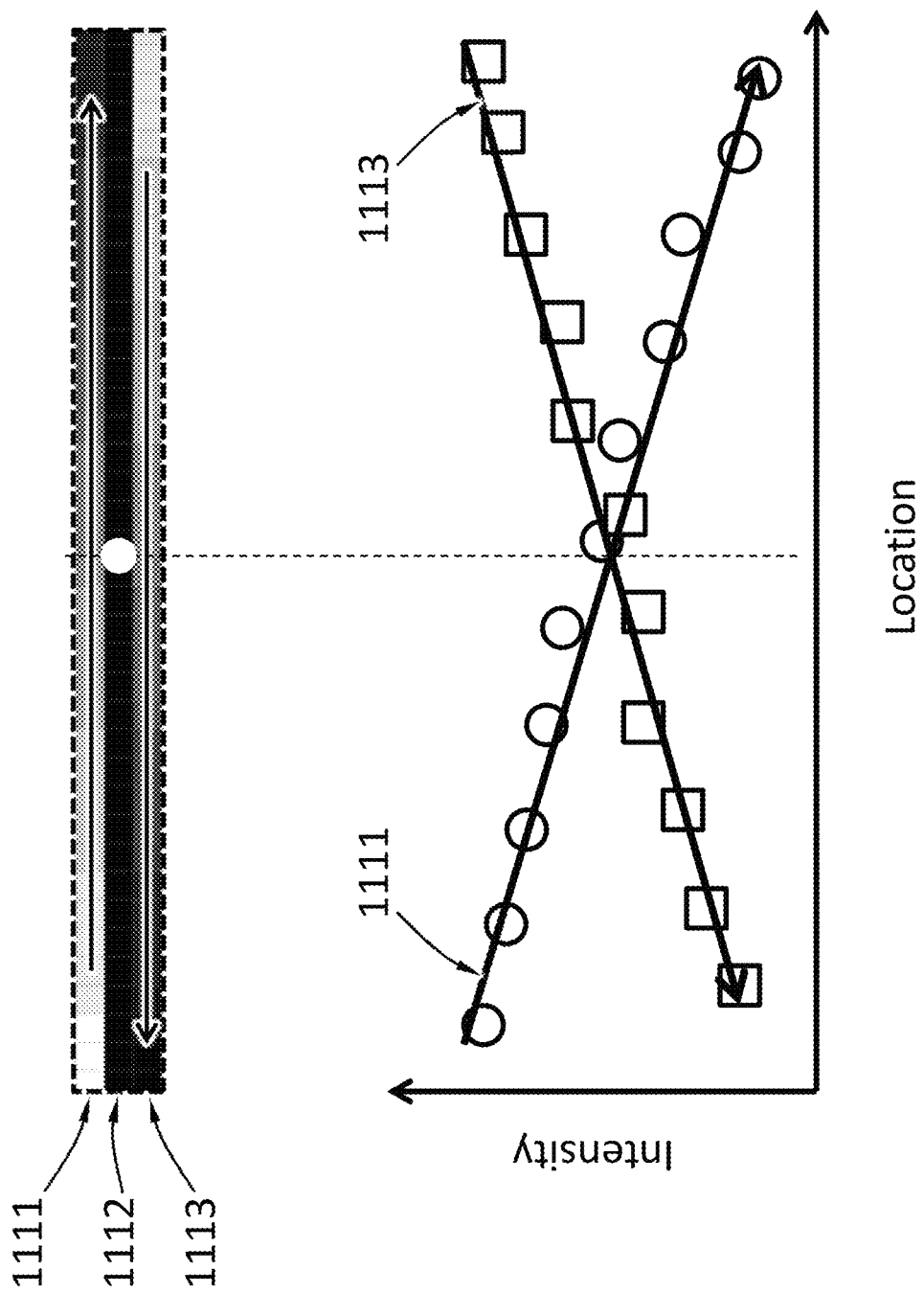
FIG. 11E schematically shows that, by linearly fitting, the intensities detected by the pixels in each of the rows as a function of location may be determined.

FIG. 11D shows a portion (marked by the dotted box in FIG. 11C) of the part 1125XA as an example. The portion includes multiple neighboring rows (e.g., 1111, 1112 and 1113) of pixels. If the cross pattern is not positioned parallel to the pixels, the pixels in these rows may detect a gradient of intensities as a function of location. As shown by FIG. 11E, by linearly fitting, the intensities detected by the pixels in each of the rows as a function of location may be determined. The point in between two rows and at which the two functions of the two rows have the same intensity is on the line 1125X. In a similar way, at least two points on the line 1125X and at least two points one the line 1125Y may be identified, thereby identifying the location of the cross pattern relative to the chip 1110.

Figure 12A:
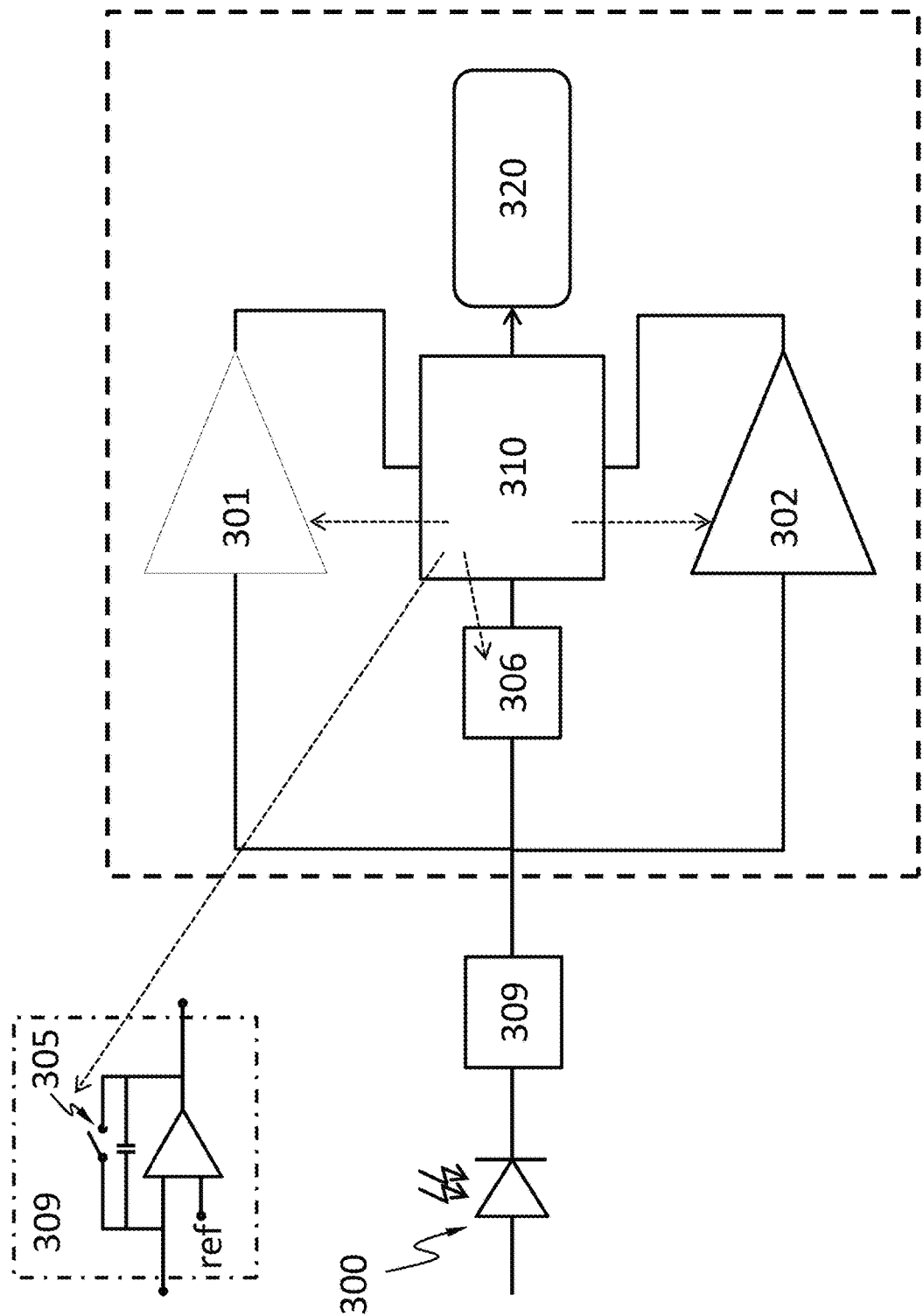
FIG. 12A and FIG. 12B each show a component diagram of an electronics system of the X-ray detector in FIG. 1A, FIG. 1B or FIG. 1C.
Figure 12B:
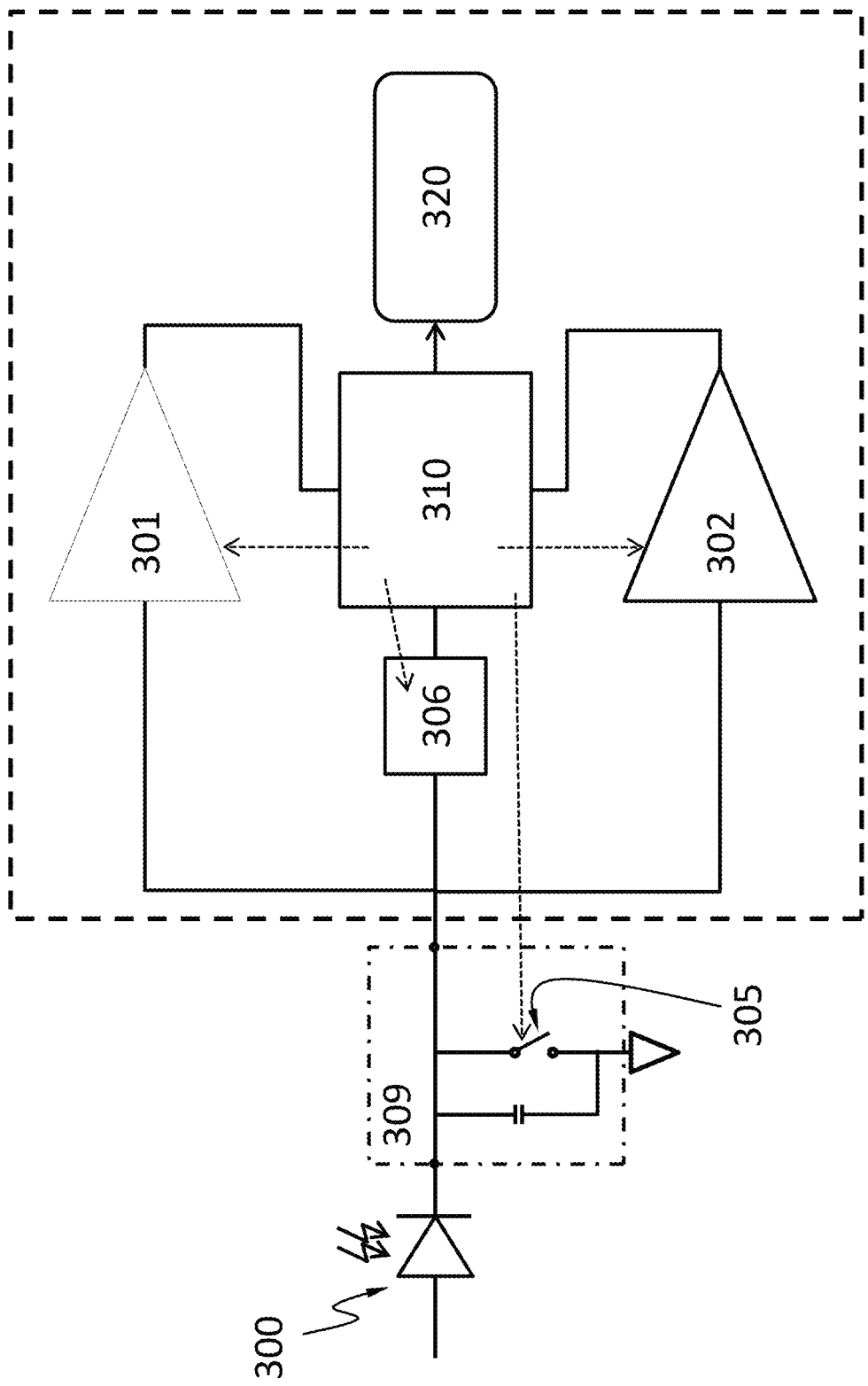

FIG. 12A and FIG. 12B each show a component diagram of the electronics system 121, according to an embodiment. The electronics system 121 may include a first voltage comparator 301, a second voltage comparator 302, a counter 320, a switch 305, a voltmeter 306 and a controller 310.

The first voltage comparator 301 is configured to compare the voltage of an electrode of a diode 300 to a first threshold. The diode may be a diode formed by the first doped region 111, one of the discrete regions 114 of the second doped region 113, and the optional intrinsic region 112. Alternatively, the first voltage comparator 301 is configured to compare the voltage of an electrical contact (e.g., a discrete portion of electrical contact 119B) to a first threshold. The first voltage comparator 301 may be configured to monitor the voltage directly, or calculate the voltage by integrating an electric current flowing through the diode or electrical contact over a period of time. The first voltage comparator 301 may be controllably activated or deactivated by the controller 310. The first voltage comparator 301 may be a continuous comparator. Namely, the first voltage comparator 301 may be configured to be activated continuously, and monitor the voltage continuously. The first voltage comparator 301 configured as a continuous comparator reduces the chance that the system 121 misses signals generated by an incident X-ray photon. The first voltage comparator 301 configured as a continuous comparator is especially suitable when the incident X-ray intensity is relatively high. The first voltage comparator 301 may be a clocked comparator, which has the benefit of lower power consumption. The first voltage comparator 301 configured as a clocked comparator may cause the system 121 to miss signals generated by some incident X-ray photons. When the incident X-ray intensity is low, the chance of missing an incident X-ray photon is low because the time interval between two successive photons is relatively long. Therefore, the first voltage comparator 301 configured as a clocked comparator is especially suitable when the incident X-ray intensity is relatively low. The first threshold may be 5-10%, 10%-20%, 20-30%, 30-40% or 40-50% of the maximum voltage one incident X-ray photon may generate in the diode or the resistor. The maximum voltage may depend on the energy of the incident X-ray photon (i.e., the wavelength of the incident X-ray), the material of the X-ray absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly, or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, \text{if } x \geq 0 \\ -x, \text{if } x \leq 0 \end{cases}.$$

The second threshold may be 200%-300% of the first threshold. The second threshold may be at least 50% of the maximum voltage one incident X-ray photon may generate in the diode or resistor. For example, the second threshold may be 100 mV, 150 mV, 200 mV, 250 mV or 300 mV. The second voltage comparator 302 and the first voltage comparator 310 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident X-ray. However, having a high speed is often at the cost of power consumption.

The counter 320 is configured to register a number of X-ray photons reaching the diode or resistor. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by the counter 320 to increase by one, if, during the time delay, the second voltage comparator 302 determines that the absolute value of the voltage equals or exceeds the absolute value of the second threshold.

The controller 310 may be configured to cause the voltmeter 306 to measure the voltage upon expiration of the time delay. The controller 310 may be configured to connect the electrode to an electrical ground, so as to reset the voltage and discharge any charge carriers accumulated on the electrode. In an embodiment, the electrode is connected to an electrical ground after the expiration of the time delay. In an embodiment, the electrode is connected to an electrical ground for a finite reset time period. The controller 310 may connect the electrode to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

Figure 13:
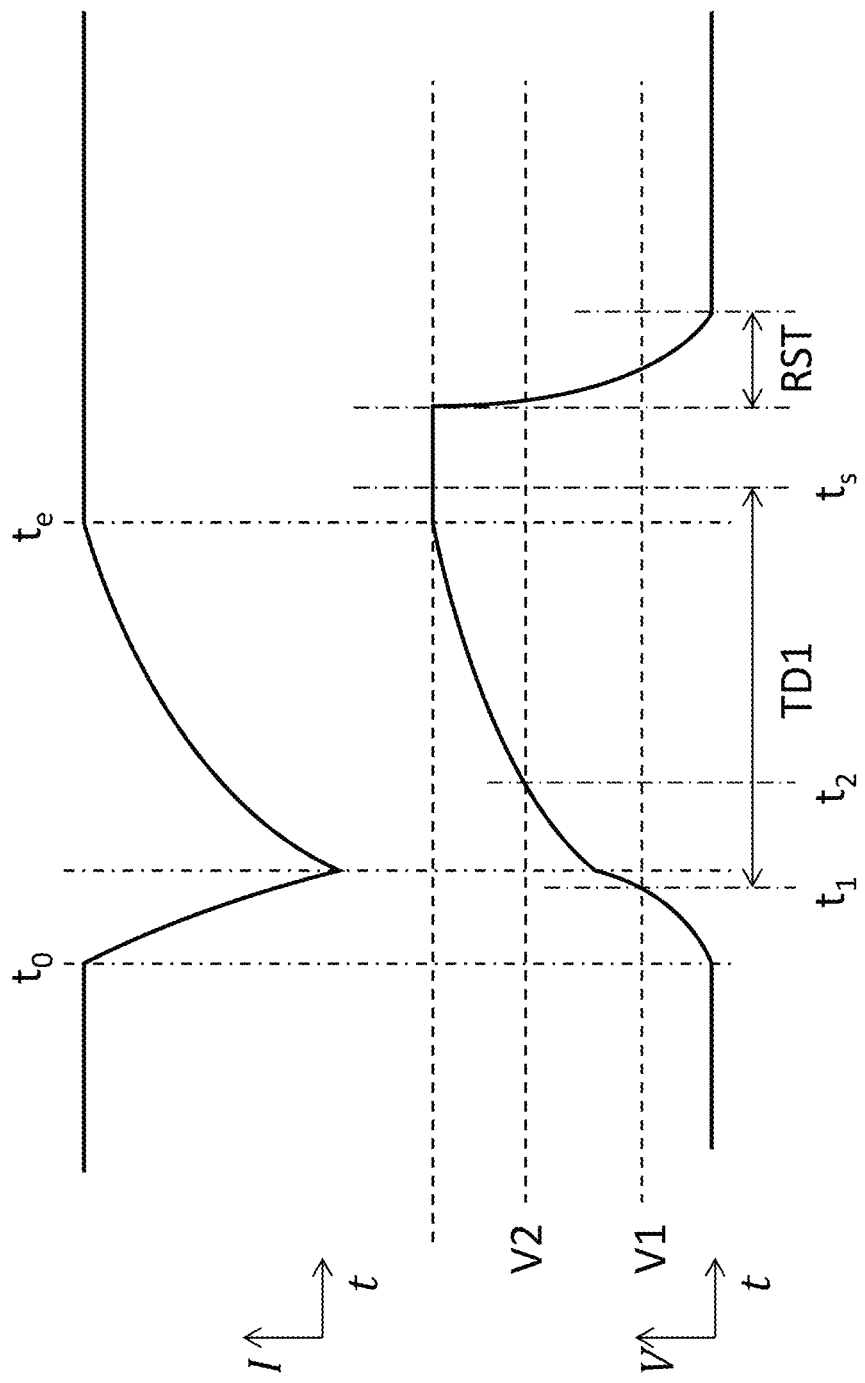
FIG. 13 schematically shows a temporal change of the electric current flowing through an electrode (upper curve) of a diode or an electrical contact of a resistor of an X-ray absorption layer exposed to X-ray, the electric current caused by charge carriers generated by an X-ray photon incident on the X-ray absorption layer, and a corresponding temporal change of the voltage of the electrode (lower curve).

The system 121 may include a capacitor module 309 electrically connected to the electrode of the diode 300 or which electrical contact, wherein the capacitor module is configured to collect charge carriers from the electrode. The capacitor module can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electrode accumulate on the capacitor over a period of time ("integration period") (e.g., as shown in FIG. 13, between $t_0$ to $t_1$, or $t_1$-$t_2$). After the integration period has expired, the capacitor voltage is sampled and then reset by a reset switch. The capacitor module can include a capacitor directly connected to the electrode.

FIG. 13 schematically shows a temporal change of the electric current flowing through the electrode (upper curve) caused by charge carriers generated by an X-ray photon incident on the diode or the resistor, and a corresponding temporal change of the voltage of the electrode (lower curve). The voltage may be an integral of the electric current with respect to time. At time $t_0$, the X-ray photon hits the diode or the resistor, charge carriers start being generated in the diode or the resistor, electric current starts to flow through the electrode of the diode or the resistor, and the absolute value of the voltage of the electrode or electrical contact starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold at time $t_2$, the controller 310 causes the number registered by the counter 320 to increase by one. At time $t_e$, all charge carriers generated by the X-ray photon drift out of the X-ray absorption layer 110. At time $t_s$, the time delay TD1 expires. In the example of FIG. 13, time $t_s$ is after time $t_e$; namely TD1 expires after all charge carriers generated by the X-ray photon drift out of the X-ray absorption layer 110. The rate of change of the voltage is thus substantially zero at $t_s$. The controller 310 may be configured to deactivate the second voltage comparator 302 at expiration of TD1 or at $t_2$, or any time in between.

The controller 310 may be configured to cause the voltmeter 306 to measure the voltage upon expiration of the time delay TD1. In an embodiment, the controller 310 causes the voltmeter 306 to measure the voltage after the rate of change of the voltage becomes substantially zero after the expiration of the time delay TD1. The voltage at this moment is proportional to the amount of charge carriers generated by an X-ray photon, which relates to the energy of the X-ray photon. The controller 310 may be configured to determine the energy of the X-ray photon based on voltage the voltmeter 306 measures. One way to determine the energy is by binning the voltage. The counter 320 may have a sub-counter for each bin. When the controller 310 determines that the energy of the X-ray photon falls in a bin, the controller 310 may cause the number registered in the sub-counter for that bin to increase by one. Therefore, the system 121 may be able to detect an X-ray image and may be able to resolve X-ray photon energies of each X-ray photon.

After TD1 expires, the controller 310 connects the electrode to an electric ground for a reset period RST to allow charge carriers accumulated on the electrode to flow to the ground and reset the voltage. After RST, the system 121 is ready to detect another incident X-ray photon. Implicitly, the rate of incident X-ray photons the system 121 can handle in the example of FIG. 13 is limited by 1/(TD1+RST). If the first voltage comparator 301 has been deactivated, the controller 310 can activate it at any time before RST expires. If the controller 310 has been deactivated, it may be activated before RST expires.

Figure 14:
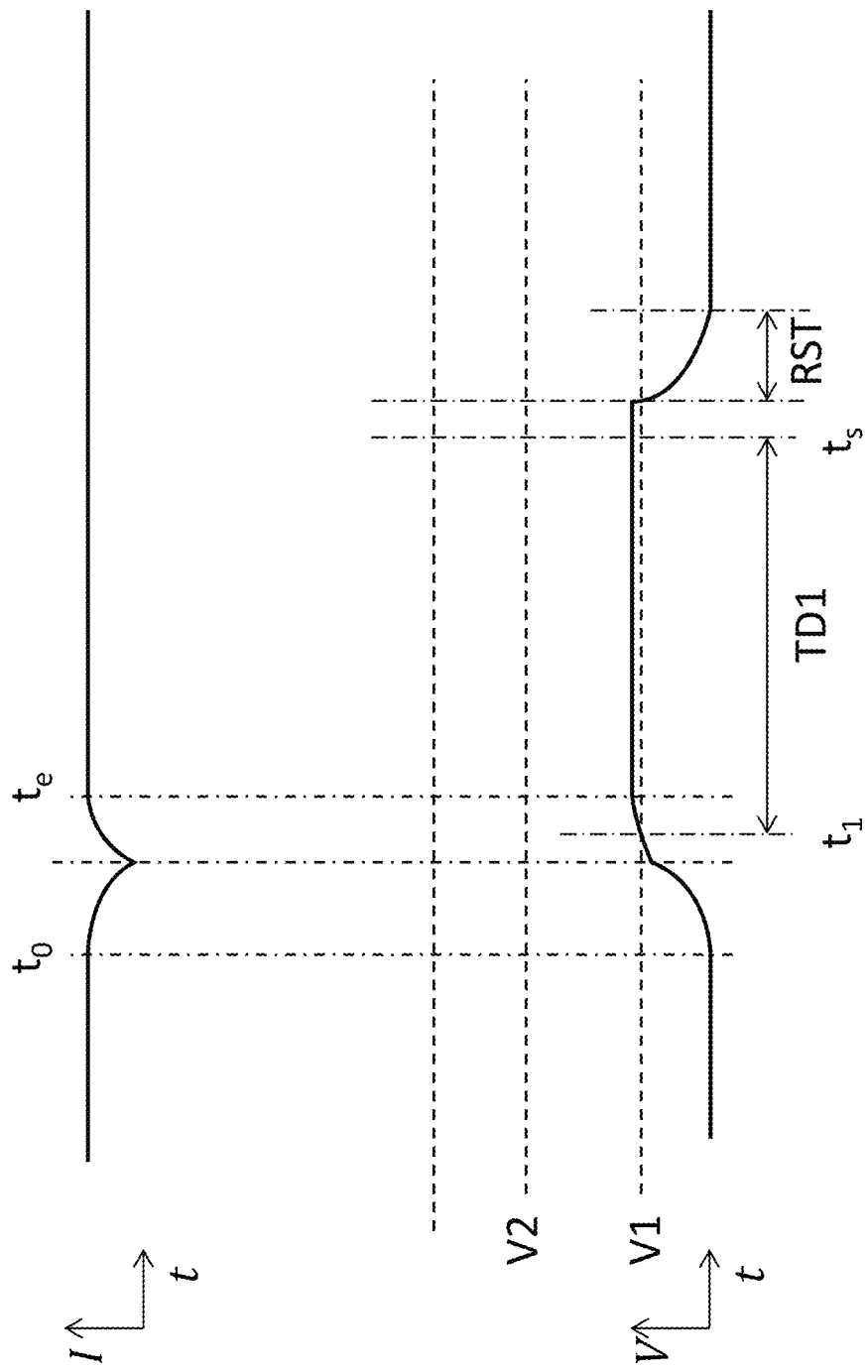
FIG. 14 schematically shows a temporal change of the electric current flowing through the electrode (upper curve) caused by noise (e.g., dark current), and a corresponding temporal change of the voltage of the electrode (lower curve), in the electronics system operating in the way shown in FIG. 8.

FIG. 14 schematically shows a temporal change of the electric current flowing through the electrode (upper curve) caused by noise (e.g., dark current, background radiation, scattered X-rays, fluorescent X-rays, shared charges from adjacent pixels), and a corresponding temporal change of the voltage of the electrode (lower curve), in the system 121 operating in the way shown in FIG. 13. At time $t_0$, the noise begins. If the noise is not large enough to cause the absolute value of the voltage to exceed the absolute value of V1, the controller 310 does not activate the second voltage comparator 302. If the noise is large enough to cause the absolute value of the voltage to exceed the absolute value of V1 at time $t_1$ as determined by the first voltage comparator 301, the controller 310 starts the time delay TD1 and the controller 310 may deactivate the first voltage comparator 301 at the beginning of TD1. During TD1 (e.g., at expiration of TD1), the controller 310 activates the second voltage comparator 302. The noise is very unlikely large enough to cause the absolute value of the voltage to exceed the absolute value of V2 during TD1. Therefore, the controller 310 does not cause the number registered by the counter 320 to increase. At time $t_e$, the noise ends. At time $t_s$, the time delay TD1 expires. The controller 310 may be configured to deactivate the second voltage comparator 302 at expiration of TD1. The controller 310 may be configured not to cause the voltmeter 306 to measure the voltage if the absolute value of the voltage does not exceed the absolute value of V2 during TD1. After TD1 expires, the controller 310 connects the electrode to an electric ground for a reset period RST to allow charge carriers accumulated on the electrode as a result of the noise to flow to the ground and reset the voltage. Therefore, the system 121 may be very effective in noise rejection.

Figure 15:
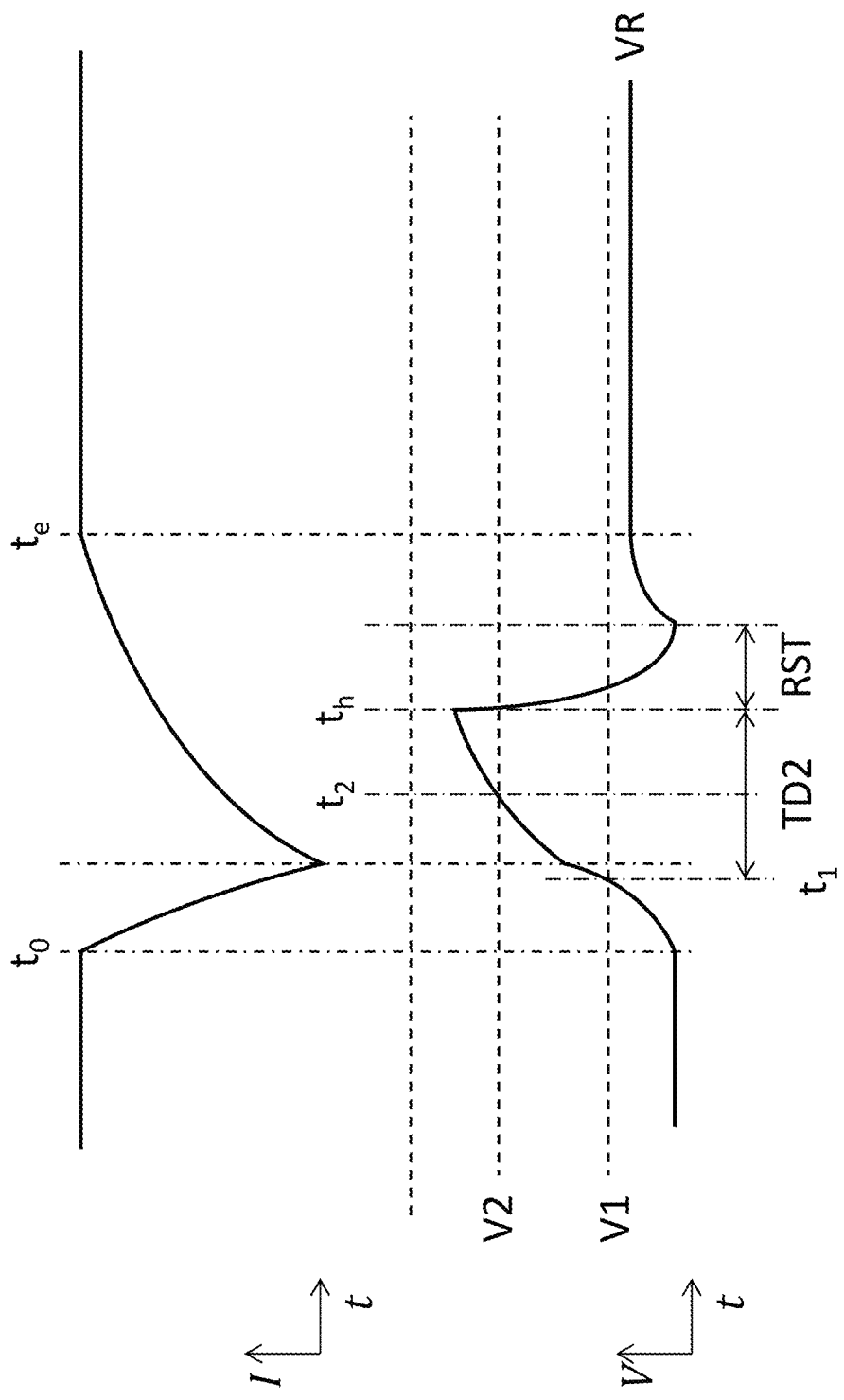
FIG. 15 schematically shows a temporal change of the electric current flowing through an electrode (upper curve) of the X-ray absorption layer exposed to X-ray, the electric current caused by charge carriers generated by an X-ray photon incident on the X-ray absorption layer, and a corresponding temporal change of the voltage of the electrode (lower curve), when the electronics system operates to detect incident X-ray photons at a higher rate.

FIG. 15 schematically shows a temporal change of the electric current flowing through the electrode (upper curve) caused by charge carriers generated by an X-ray photon incident on the diode or the resistor, and a corresponding temporal change of the voltage of the electrode (lower curve), when the system 121 operates to detect incident X-ray photons at a rate higher than 1/(TD1+RST). The voltage may be an integral of the electric current with respect to time. At time $t_0$, the X-ray photon hits the diode or the resistor, charge carriers start being generated in the diode or the resistor, electric current starts to flow through the electrode of the diode or the electrical contact of resistor, and the absolute value of the voltage of the electrode or the electrical contact starts to increase. At time $t_1$, the first voltage comparator 301 determines that the absolute value of the voltage equals or exceeds the absolute value of the first threshold V1, and the controller 310 starts a time delay TD2 shorter than TD1, and the controller 310 may deactivate the first voltage comparator 301 at the beginning of TD2. If the controller 310 is deactivated before $t_1$, the controller 310 is activated at $t_1$. During TD2 (e.g., at expiration of TD2), the controller 310 activates the second voltage comparator 302. If during TD2, the second voltage comparator 302 determines that the absolute value of the voltage equals or exceeds the absolute value of the second threshold at time $t_2$, the controller 310 causes the number registered by the counter 320 to increase by one. At time $t_e$, all charge carriers generated by the X-ray photon drift out of the X-ray absorption layer 110. At time $t_h$, the time delay TD2 expires. In the example of FIG. 15, time $t_h$ is before time $t_e$; namely TD2 expires before all charge carriers generated by the X-ray photon drift out of the X-ray absorption layer 110. The rate of change of the voltage is thus substantially non-zero at $t_h$. The controller 310 may be configured to deactivate the second voltage comparator 302 at expiration of TD2 or at $t_2$, or any time in between.

The controller 310 may be configured to extrapolate the voltage at $t_e$ from the voltage as a function of time during TD2 and use the extrapolated voltage to determine the energy of the X-ray photon.

After TD2 expires, the controller 310 connects the electrode to an electric ground for a reset period RST to allow charge carriers accumulated on the electrode to flow to the ground and reset the voltage. In an embodiment, RST expires before $t_e$. The rate of change of the voltage after RST may be substantially non-zero because all charge carriers generated by the X-ray photon have not drifted out of the X-ray absorption layer 110 upon expiration of RST before $t_e$. The rate of change of the voltage becomes substantially zero after $t_e$ and the voltage stabilized to a residue voltage VR after $t_e$. In an embodiment, RST expires at or after $t_e$, and the rate of change of the voltage after RST may be substantially zero because all charge carriers generated by the X-ray photon drift out of the X-ray absorption layer 110 at $t_e$. After RST, the system 121 is ready to detect another incident X-ray photon. If the first voltage comparator 301 has been deactivated, the controller 310 can activate it at any time before RST expires. If the controller 310 has been deactivated, it may be activated before RST expires.

Figure 16:
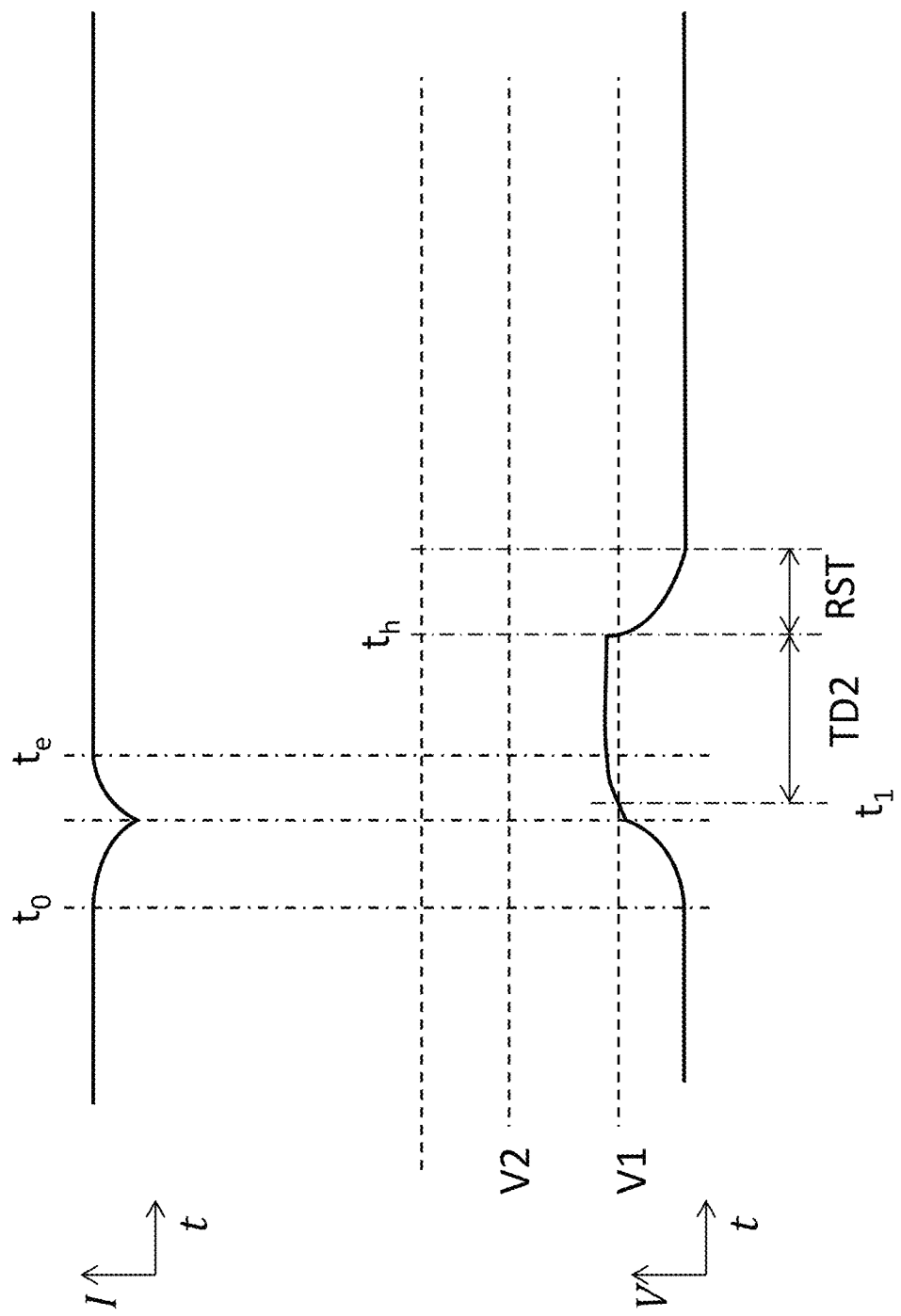
FIG. 16 schematically shows a temporal change of the electric current flowing through the electrode (upper curve) caused by noise (e.g., dark current), and a corresponding temporal change of the voltage of the electrode (lower curve), in the electronics system operating in the way shown in FIG. 12.

FIG. 16 schematically shows a temporal change of the electric current flowing through the electrode (upper curve) caused by noise (e.g., dark current, background radiation, scattered X-rays, fluorescent X-rays, shared charges from adjacent pixels), and a corresponding temporal change of the voltage of the electrode (lower curve), in the system 121 operating in the way shown in FIG. 15. At time $t_0$, the noise begins. If the noise is not large enough to cause the absolute value of the voltage to exceed the absolute value of V1, the controller 310 does not activate the second voltage comparator 302. If the noise is large enough to cause the absolute value of the voltage to exceed the absolute value of V1 at time $t_1$ as determined by the first voltage comparator 301, the controller 310 starts the time delay TD2 and the controller 310 may deactivate the first voltage comparator 301 at the beginning of TD2. During TD2 (e.g., at expiration of TD2), the controller 310 activates the second voltage comparator 302. The noise is very unlikely large enough to cause the absolute value of the voltage to exceed the absolute value of V2 during TD2. Therefore, the controller 310 does not cause the number registered by the counter 320 to increase. At time $t_e$, the noise ends. At time $t_h$, the time delay TD2 expires. The controller 310 may be configured to deactivate the second voltage comparator 302 at expiration of TD2. After TD2 expires, the controller 310 connects the electrode to an electric ground for a reset period RST to allow charge carriers accumulated on the electrode as a result of the noise to flow to the ground and reset the voltage. Therefore, the system 121 may be very effective in noise rejection.

Figure 17:
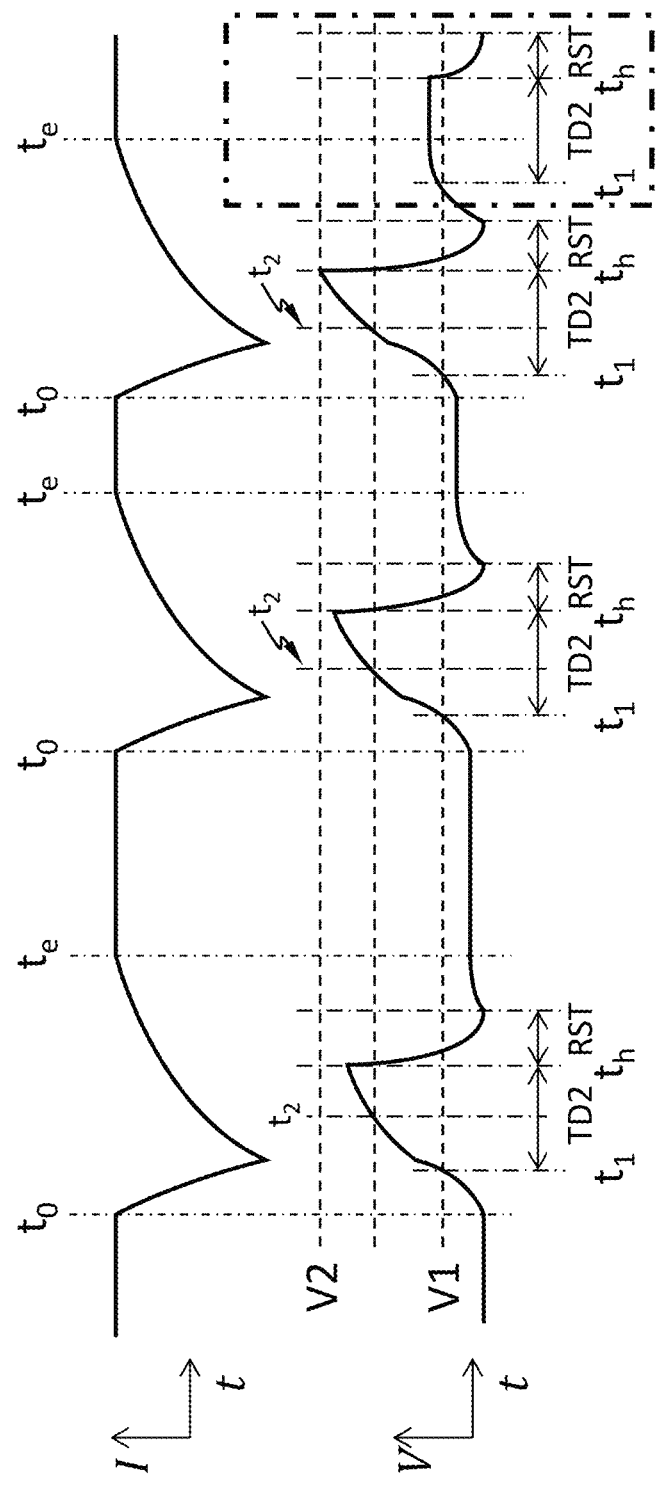
FIG. 17 schematically shows a temporal change of the electric current flowing through the electrode (upper curve) caused by charge carriers generated by a series of X-ray photons incident on the X-ray absorption layer, and a corresponding temporal change of the voltage of the electrode, in the electronics system operating in the way shown in FIG. 12 with RST expires before $t_e$.

FIG. 17 schematically shows a temporal change of the electric current flowing through the electrode (upper curve) caused by charge carriers generated by a series of X-ray photons incident on the diode or the resistor, and a corresponding temporal change of the voltage of the electrode (lower curve), in the system 121 operating in the way shown in FIG. 15 with RST expires before $t_e$. The voltage curve caused by charge carriers generated by each incident X-ray photon is offset by the residue voltage before that photon. The absolute value of the residue voltage successively increases with each incident photon. When the absolute value of the residue voltage exceeds V1 (see the dotted rectangle in FIG. 17), the controller starts the time delay TD2 and the controller 310 may deactivate the first voltage comparator 301 at the beginning of TD2. If no other X-ray photon incidence on the diode or the resistor during TD2, the controller connects the electrode to the electrical ground during the reset time period RST at the end of TD2, thereby resetting the residue voltage. The residue voltage thus does not cause an increase of the number registered by the counter 320.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
   obtaining a third image from a first X-ray detector when the first X-ray detector and a second X-ray detector are misaligned;
   obtaining a fourth image from the second X-ray detector when the first X-ray detector and the second X-ray detector are misaligned;
   determining, based on a shift between a first image and the third image and a shift between a second image and the fourth image, a misalignment between the first X-ray detector and the second X-ray detector;
   wherein the first image is an image the first X-ray detector should capture if the first and the second X-ray detectors are aligned;
   wherein the second image is an image the second X-ray detector should capture if the first and the second X-ray detectors are aligned.

2. The method of claim 1, wherein the first X-ray detector and the second X-ray detector are stacked.

3. The method of claim 2, wherein the first and third images are formed from a beam of X-ray directed to the first X-ray detector.

4. The method of claim 3, wherein a part of the beam is absorbed by the first X-ray detector and another part of the beam passes through the first X-ray detector.

5. The method of claim 2, wherein the first and third images are formed from a scene of X-ray.

6. The method of claim 2, wherein the first and third images are images of one or more structures of the second X-ray detector.

7. The method of claim 6, wherein the one or more structures are gaps between pixels.

8. The method of claim 6, wherein the one or more structures are solder bumps.

9. The method of claim 1, wherein the first X-ray detector and the second X-ray detector are arranged side by side.

10. The method of claim 9, wherein the first and third images are formed from a first beam of X-ray directed to the first X-ray detector.

11. The method of claim 9, wherein the first image is an image of a part of a scene of X-ray.

12. The method of claim 1, wherein the first X-ray detector has multiple pixels.

13. The method of claim 1, wherein the first X-ray detector comprises:
    an X-ray absorption layer comprising an electrode;
    an electronics layer comprising an electronics system.

14. The method of claim 13, wherein the electronics system comprises:
    a first voltage comparator configured to compare a voltage of the electrode to a first threshold;
    a second voltage comparator configured to compare the voltage to a second threshold;
    a counter configured to register a number of X-ray photons reaching the X-ray absorption layer;
    a controller;
    wherein the controller is configured to start a time delay from a time at which the first voltage comparator determines that an absolute value of the voltage equals or exceeds an absolute value of the first threshold;
    wherein the controller is configured to activate the second voltage comparator during the time delay;
    wherein the controller is configured to cause the number registered by the counter to increase by one, if the second voltage comparator determines that an absolute value of the voltage equals or exceeds an absolute value of the second threshold.

15. The method of claim 14, wherein the electronics system further comprises a capacitor module electrically connected to the electrode of the X-ray absorption layer, wherein the capacitor module is configured to collect charge carriers from the electrode of the X-ray absorption layer.

16. The method of claim 14, wherein the controller is configured to activate the second voltage comparator at a beginning or expiration of the time delay.

17. The method of claim 14, wherein the electronics system further comprises a voltmeter, wherein the controller is configured to cause the voltmeter to measure the voltage upon expiration of the time delay.

18. The method of claim 14, wherein the controller is configured to determine an X-ray photon energy based on a value of the voltage measured upon expiration of the time delay.

19. The method of claim 14, wherein the controller is configured to connect the electrode of the X-ray absorption layer to an electrical ground.

20. The method of claim 14, wherein a rate of change of the voltage is substantially zero at expiration of the time delay.

21. The method of claim 14, wherein a rate of change of the voltage is substantially non-zero at expiration of the time delay.

22. The method of claim 14, wherein the X-ray absorption layer comprises a diode.

* * * * *